US009649382B2

(12) United States Patent
Joabsson et al.

(10) Patent No.: US 9,649,382 B2
(45) Date of Patent: *May 16, 2017

(54) TOPICAL BIOADHESIVE FORMULATIONS

(71) Applicant: CAMURUS AB, Lund (SE)

(72) Inventors: Fredrik Joabsson, Lund (SE); Margareta Linden, Lund (SE); Krister Thuresson, Lund (SE); Fredrik Tiberg, Lund (SE)

(73) Assignee: CAMURUS AB (SE)

( * ) Notice: Subject to any disclaimer, the term of this patent is extended or adjusted under 35 U.S.C. 154(b) by 181 days.

This patent is subject to a terminal disclaimer.

(21) Appl. No.: 14/138,704

(22) Filed: Dec. 23, 2013

(65) Prior Publication Data
US 2014/0186279 A1 Jul. 3, 2014

Related U.S. Application Data

(63) Continuation-in-part of application No. 11/795,242, filed as application No. PCT/GB2005/004746 on Dec. 9, 2005, now Pat. No. 8,920,782.

(30) Foreign Application Priority Data

Jan. 14, 2005 (GB) .................................. 0500807.3
Apr. 18, 2005 (GB) .................................. 0507811.8
Jun. 6, 2005 (WO) ................ PCT/GB2005/002217

(51) Int. Cl.
A61K 8/00 (2006.01)
A61K 47/24 (2006.01)
A61K 33/16 (2006.01)
A61K 31/198 (2006.01)
A61K 8/02 (2006.01)
A61Q 19/00 (2006.01)
A61K 8/37 (2006.01)
A61K 31/155 (2006.01)
A61K 31/196 (2006.01)
A61K 31/355 (2006.01)
(Continued)

(52) U.S. Cl.
CPC ............ A61K 47/24 (2013.01); A61K 8/0216 (2013.01); A61K 8/375 (2013.01); A61K 8/553 (2013.01); A61K 9/006 (2013.01); A61K 9/0014 (2013.01); A61K 9/0043 (2013.01); A61K 9/0063 (2013.01); A61K 9/7015 (2013.01); A61K 31/155 (2013.01); A61K 31/196 (2013.01); A61K 31/198 (2013.01); A61K 31/355 (2013.01); A61K 31/416 (2013.01); A61K 31/4468 (2013.01); A61K 31/5513 (2013.01); A61K 31/568 (2013.01); A61K 31/573 (2013.01); A61K 31/7056 (2013.01); A61K 33/16 (2013.01); A61K 47/10 (2013.01); A61K 47/14 (2013.01); A61K 47/22 (2013.01); A61Q 19/00 (2013.01); A61K 2800/10 (2013.01); A61Q 17/04 (2013.01)

(58) Field of Classification Search
CPC .......... A61K 8/55; A61K 47/24; A61K 33/16; A61K 31/198; A61K 31/568; A61K 8/0216; A61K 8/553; A61K 8/375; A61K 9/0014; A61K 47/22; A61K 9/7015; A61K 9/0043; A61K 9/006; A61K 9/0063; A61K 31/446; A61Q 19/00
USPC ........................................................ 424/59
IPC .................. A61K 47/24,33/16, 31/198, 31/568, 8/0216, 8/553, 8/375, 9/0014, 47/22, 9/7015, 9/0043, 9/006, 9/0063, 31/4468, 31/7056, 47/14, 31/155, 31/196, 31/5513, 47/10, 31/416, 31/355, 31/573, 2800/10, 31/446; A61Q 19/00, 17/04
See application file for complete search history.

(56) References Cited

U.S. PATENT DOCUMENTS 4,938,763 A 7/1990 Dunn et al.
5,340,802 A 8/1994 Shiosaki et al.
(Continued)

FOREIGN PATENT DOCUMENTS

EP 1600162 11/2005
JP 2001-058955 A 3/2001
(Continued)

OTHER PUBLICATIONS

About Sandostatin: Proven Control of GH, 1GF-1 and Gastrointestinal Hormone, from www.sandostatin.com/about.sandostatin/index.html and linked documents.
(Continued)

Primary Examiner — Snigdha Maewall
(74) Attorney, Agent, or Firm — J.A. Lindeman & Co., PLLC

(57) ABSTRACT

The present invention relates to topical bioadhesive formulations comprising low viscosity, non-liquid crystalline, mixtures of:
a) at least one neutral diacyl lipid and/or at least one tocopherol;
b) at least one phospholipid;
c) at least one biocompatible, oxygen containing, low viscosity organic solvent;
wherein at least one bioactive agent is dissolved or dispersed in the low viscosity mixture and wherein the pre-formulation forms, or is capable of forming, at least one liquid crystalline phase structure upon contact with an aqueous fluid. The invention additionally relates to a method of delivery of an active agent comprising administration of a preformulation of the invention, a method of treatment comprising administration of a preformulation of the invention and the use of a preformulation of the invention in a method for the manufacture of a medicament.

23 Claims, 7 Drawing Sheets

Figure 1:
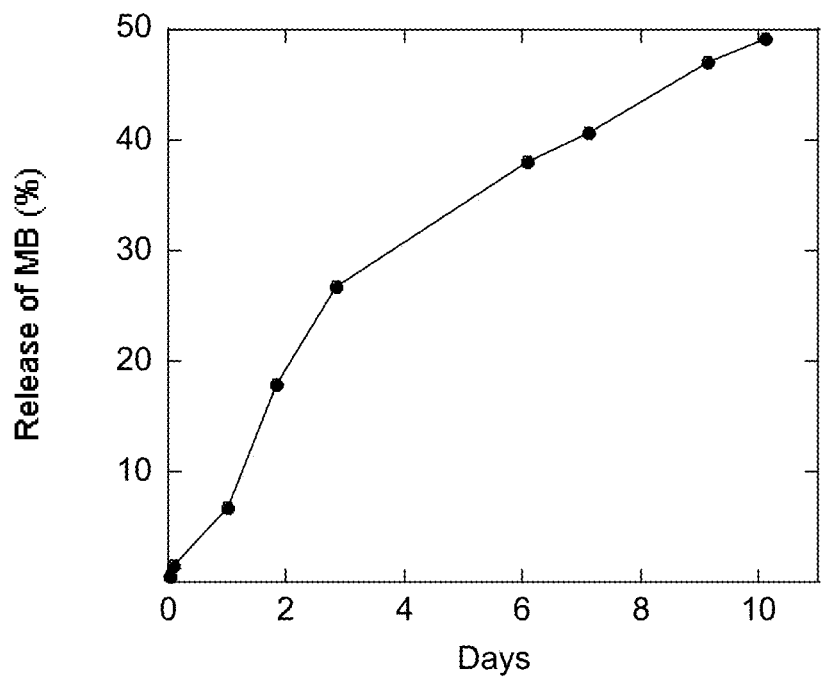

(51) Int. Cl.

| | | |
|---|---|---|
| A61K 31/416 | (2006.01) | |
| A61K 31/4468 | (2006.01) | |
| A61K 31/5513 | (2006.01) | |
| A61K 31/573 | (2006.01) | |
| A61K 31/7056 | (2006.01) | |
| A61K 47/10 | (2017.01) | |
| A61K 47/14 | (2017.01) | |
| A61K 9/00 | (2006.01) | |
| A61K 47/22 | (2006.01) | |
| A61K 9/70 | (2006.01) | |
| A61K 8/55 | (2006.01) | |
| A61K 31/568 | (2006.01) | |
| A61Q 17/04 | (2006.01) | |

(56) References Cited

U.S. PATENT DOCUMENTS

| | | | |
|---|---|---|---|
| 5,480,656 | A | 1/1996 | Okada et al. |
| 5,531,925 | A | 7/1996 | Landh et al. |
| 5,639,480 | A | 6/1997 | Bodmer et al. |
| 5,776,885 | A | 7/1998 | Orsolini et al. |
| 5,807,573 | A * | 9/1998 | Ljusberg-Wahren ............ A61K 9/1274 424/450 |
| 5,955,502 | A * | 9/1999 | Hansen ............ A61K 9/0014 424/407 |
| 6,011,067 | A | 1/2000 | Hersh |
| 6,066,328 | A | 5/2000 | Ribier et al. |
| 6,113,943 | A | 9/2000 | Okada et al. |
| 6,228,383 | B1 | 5/2001 | Hansen et al. |
| 6,458,924 | B2 | 10/2002 | Knudsen et al. |
| 6,464,987 | B1 * | 10/2002 | Fanara ............ A61K 9/0019 424/400 |
| 8,097,239 | B2 | 1/2012 | Johnsson et al. |
| 8,182,834 | B2 | 5/2012 | Johnsson et al. |
| 8,187,629 | B2 | 5/2012 | Barauskas et al. |
| 8,236,292 | B2 | 8/2012 | Thuresson et al. |
| 8,236,755 | B2 | 8/2012 | Thuresson et al. |
| 2002/0026027 | A1 | 2/2002 | Ansell |
| 2003/0022242 | A1 | 1/2003 | Anderson |
| 2004/0018241 | A1 | 1/2004 | Houze et al. |
| 2004/0201117 | A1 | 10/2004 | Anderson |
| 2005/0136059 | A1 | 6/2005 | Thorpe et al. |
| 2006/0073203 | A1 | 4/2006 | Ljusberg-Wahren et al. |
| 2007/0080323 | A1 | 4/2007 | Joabsson et al. |
| 2007/0110777 | A1 | 5/2007 | Joabsson et al. |
| 2007/0134336 | A1 | 6/2007 | Worle et al. |
| 2007/0231374 | A1 | 10/2007 | Tiberg et al. |
| 2008/0124394 | A1 | 5/2008 | Johnsson et al. |
| 2008/0146490 | A1 | 6/2008 | Joabsson et al. |
| 2008/0161276 | A1 | 7/2008 | Johnsson et al. |
| 2008/0214995 | A1 | 9/2008 | Boyd et al. |
| 2008/0274176 | A1 | 11/2008 | Johnsson et al. |
| 2009/0069221 | A1 | 3/2009 | Joabsson et al. |
| 2009/0170782 | A1 | 7/2009 | Joabsson et al. |
| 2010/0210519 | A1 | 8/2010 | Johnsson et al. |
| 2011/0230569 | A1 | 9/2011 | Nistor et al. |
| 2012/0028890 | A1 | 2/2012 | Nistor et al. |
| 2012/0269772 | A1 | 10/2012 | Thuresson et al. |

FOREIGN PATENT DOCUMENTS

| | | |
|---|---|---|
| WO | WO 93/06921 A1 | 4/1993 |
| WO | WO 95/34287 A1 | 12/1995 |
| WO | WO 97/13528 A1 | 4/1997 |
| WO | WO 98/47487 A1 | 10/1998 |
| WO | WO 02/02716 A2 | 1/2002 |
| WO | WO 02/066014 A2 | 8/2002 |
| WO | WO 02/068561 A2 | 9/2002 |
| WO | WO 02/068562 A2 | 9/2002 |
| WO | WO 03/002136 A2 | 1/2003 |
| WO | WO 03/057235 A2 | 7/2003 |
| WO | WO 2004/087215 A1 | 10/2004 |
| WO | WO 2005/014162 A1 | 2/2005 |
| WO | WO 2005/021022 A2 | 3/2005 |
| WO | WO 2005/046642 A1 | 5/2005 |
| WO | WO 2005/048952 A2 | 6/2005 |
| WO | WO 2005/063213 A1 | 7/2005 |
| WO | WO 2005/070394 A2 | 8/2005 |
| WO | WO 2005/117830 A1 | 12/2005 |
| WO | WO 2006/075123 A1 | 7/2006 |
| WO | WO 2006/075124 A1 | 7/2006 |
| WO | WO 2006/075125 A1 | 7/2006 |
| WO | WO 2006/077362 A1 | 7/2006 |
| WO | WO 2006/131730 A1 | 12/2006 |
| WO | WO 2008/152401 A1 | 12/2008 |
| WO | WO 2009/024795 A1 | 2/2009 |
| WO | WO 2009/024797 A1 | 2/2009 |
| WO | WO 2010/020794 A1 | 2/2010 |

OTHER PUBLICATIONS

"Acromegaly" from www.niddk.nil.gov/health/endo/pubs/acro/acro.htm.

American Peptide Company, Product Details "Somatostatin and analogs," from www.americanpeptide.com/.

N. Ardjomand et al., "Expression of Somatostatin Receptors in uveal melanomas," Inv. Opthalmol. & Vis. Sci., 2003, vol. 44, No. 3, pp. 980-987.

Barauskas et al., Pharmaceutical Nanotechnology, "Interactions of lipid-based liquid crystalline nanoparticles with model and cell membranes," International Journal of Pharmaceutics 391 (2010) pp. 284-291.

R. Berges, "Eligard: Pharmacokinetics, Effect on Testosterone and PSA Levels and Tolerability," European Urology Supplements, 2005, vol. 4, pp. 20-25.

Chang, J., "Use of GnRH agonists in the treatment of hyperandrogenism and hirsutism," print out from http://patients.uptodate.com.

P. Chanson et al., "Comparison of octreotide acetate LAR and lanreptide SR in patients with acromegaly," Clin. Endocrinology, 2001, vol. 54, No. 1, pp. 11-13, (Abstract only).

Comets et al., "Non parametric analysis of the absorption profile of octreotide in rabbits from long-acting release formulation OncoLAR," J. Controlled Release 59:197-205 (1999).

F. Dall'Antonia, "Structure determination of organo-silicon compounds.", pp. 6 to 8 from http://shelx.uni-ac.gwdg.de/-fabio/endwkcon.htm.

Definition of analog from http://cancerweb.ncl.ac.uk!omd/about.html, pp. 1-5. Accessed Jul. 7, 2005.

B. L. Erstad, "Octreotide for acute variceal bleeding," Ann. Pharmacother., 2001, vol. 35, No. 5, pp. 618-626. (Abstract only).

A. K. Flogstatin et al., "Sandostatin LAR in acromegalic patients: long term treatment," J. Clinical Endocrinology & Metabolism, 1997, vol. 82, No. 1, pp. 23-28.

G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.

H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.

Indications and Usage of Eligard, pp. 1-5, print out from http:ffw-ww.rxlist.com.

Information About Buprenorphine Therapy, print out from http://buprenorphine.samhsa.gov/about.html, pp. 1-4.

Information on Goserelin Acetate print out form http://www.bachem.com/.

Information on Goserelin Subcutaneous, Monograph—Goserelin Acetate, pp. 1-7, print out form www.medscape.com.

Information on Leuprolide Intramuscular, Monograph—Leuprolide Acetate, pp. 1-20, print out for www.medscape.com.

Information on Leuprolide (3 Month) Intramuscular, Monograph—Leuprolide Acetate, pp. 1-20, print out from www.medscape.com.

(56) References Cited

OTHER PUBLICATIONS

Invitrogen, "Pluronic F-127," Molecular Probes Invitrogen Detection Technologies, pp. 1-2, 2008.
Johnsson et al., "Physicochemical and Drug Delivery Aspects of Lipid-Based Liquid Crystalline Nanoparticles: A Case Study of Intravenously Administered Propofol," Journal of Nanoscience and Nanotechnology, vol. 6, No. 9/10, pp. 3017-3024, 2006.
Kamo, et al., "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.
J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).
L. M. Knudsen, "Glucagon-like Peptide-1: The Basis of a New Class of Treatment for Type 2 Diabetes," J. Med. Chem. (2004), vol. 47, pp. 4128-4134.
L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.
I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.
"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.
Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.
Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008.
Martel et al., "Enzyme Linked !mmunosorbent Assay (EUSA) Method for the Determination of TH0318, a New GLP-1 Analogue in Development for Diabetes," Poster.
MSDS for Ethylene Glycol and Abbreviations used in Toxicity data.
Novartis Pharmaceuticals Corporation, "Sansdostatin LAR Depot (octreotide acetate for injectable suspension)", pp. 1-19.
PDR Information on Eligard 30 mg (Sanofi-Synthelabo), print out from www.Drugs.com, pp. 1-14.
Pharmaceutical Information on LUPRON DEPOT, print out from www.rxmed.com, pp. 1-8.
Product Information on Zoladex Goserelin Acetate Implant (Equivalent to 10.8 mg goserelin).
Product Specification of Leuprolide by GL Biochem, print out from http://www.glschina.com.
Published Data Provided by Sandostatin LAR "The Latest Research and Treatment Information for Pituitary Disorders" from http://www.sandostatin.com/published data/index.html.
O. Sartor "Eligard: Leuprolide Acetate in a Novel Sustained-Release Delivery System," Urology, 2003, vol. 61, (Supplement 2A), pp. 25-31.
K. J. Schuh et al., "Onset, magnitude and duration of opioid blockade produced by buprenorphine and naltrexone in humans," Psychopharmacology, (Berl), Jul. 1999, vol. 145, No. 2, pp. 162-174 (Abstract only).
"Setting new standards of care," Mixing and Administration instructions for Sandostatin LAR.
Tiberg et al., "Drug delivery applications of non-lamellar liquid crystalline phases and nanoparticles", J. Drug Del Sci. Tech., 21(1) pp. 101-109, 2011.
Treating Acromegaly, from http://www.sandostatin.com/lreating acromegaly/index.html and linked documents.
Welin et al., "High-dose treatment with a long-acting somatostatin analogue in patients with advanced midgut carcinoid tumours," 2004, Society of the European Journal of Endocrinology, vol. 151, pp. 107-112.
Wermuth, Pure and Appl. Chem, 1998, 70, 1129-1143.
E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only).
E. A. Woltering, "A discussion on the utility of various routes of administration of octreotide acetate," from http://www.carcinoid.org/medpro/docs/WoltPump2005.htm.
Tiberg et al., "Treatment of oral mucositis pain by a bioadhesive barrier forming lipid solution," Camurus (attached hereto as Annex 3 to Evidentiary Declaration Under 37 C.F.R. §1.132 of Fredrik Tiberg).
Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. §1.132 of Fredrik Tiberg).
Svanberg et al., "A New Preventive Strategy Using a Bioadhesive Oromucosal Lipid Solution and Oral Cryotherapy to Protect the Oral Cavity—and Reduce the Need for Total Parenteral Nutrition (Tpn) for Patients Undergoing Autologous Stemcell Transplantation," Support Care Cancer 18(Suppl 3):S114-S115, at Abstract 08-076 (2010) (attached hereto as Annex 5 to Evidentiary Declaration Under 37 C.F.R. §1.132 of Fredrik Tiberg).
L. M. Grant & F. Tibert, "Normal and Lateral Forces between Lipid Covered Solids in Solution: Correlation with Layer Packing and Structure," Biophysical Journal, 2002, vol. 82, pp. 1373-1385.
B.A. Hills, "Surface-active phosphilipid: a Pandora's box of clinical applications. Part II. Barrier and lubricating properties," Internal Medicine Journal, 2002, vol. 32, pp. 242-251.
A Sturm & A. U. Dignass, "Modulation of gastroentestinal wound repair and inflammation by phospholipids," Biochimica et Biophysica Acta, 2002, vol. 1582, pp. 282-288.
F. Kesisoglou et al., "Liposomal Formulations of Inflammatory Bowel Disease Drugs: Local Versus Systemic Drug Delivery in a Rat Model," Pharma. Res., 2005, vol. 22, No. 8, pp. 1320-1330.
W. Stremmel et al., "Retarded release phosphatidylcholine benefits patients with chronic active ulcerative colitis," Gut, 2005, vol. 54, pp. 966-971.
P. R. Gibson & J. G. Muir, "Reinforcing the mucus: a new therapeutic approach for ulcerative colitis," Gut, 2005, vol. 54, pp. 900-903.
J. C. Sha et al., "Cubic phase gels as drug delivery systems," Advanced Drug Delivery Reviews, 2001, vol. 47, pp. 229-250.
FDA's 510(k) Summary of Camurus AB, episil® K101769.
International Search Report of PCT/GB2005/004745 dated May 8, 2006.
International Preliminary Report on Patentability of PCT/GB2005/004745 dated Jul. 20, 2007.
Written Opinion of PCT/GB2005/004745 dated May 8, 2006.
International Search Report of PCT/GB2005/04748 dated Mar. 23, 2006.
International Preliminary Report on Patentability of PCT/GB2005/04748 dated Mar. 12, 2007.
Written Opinion of PCT/GB2005/04748 dated Mar. 23, 2006.
International Search Report of PCT/GB2005/04752 dated Mar. 17, 2006.
International Preliminary Report on Patentability of PCT/GB2005/04752 dated Mar. 12, 2007.
Written Opinion of PCT/GB2005/04752 dated Mar. 17, 2006.
International Search Report of PCT/GB2005/004746 dated Mar. 16, 2006.
International Preliminary Report on Patentability and Written Opinion of PCT/GB2005/004746 dated Jul. 17, 2007.
International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002035 dated Oct. 6, 2008.

(56) References Cited

OTHER PUBLICATIONS

International Preliminary Report on Patentability of PCT/GB2008/002035 Dec. 17, 2009.
Written Opinion of PCT/GB2008/002035 dated Oct. 6, 2008.
International Search Report of PCT/GB2008/002857 dated Jan. 28, 2009.
International Preliminary Report on Patentability and Written Opinion of PCT/GB2008/002857 dated Feb. 24, 2010.
International Search Report of PCT/GB2009/002054 dated Nov. 30, 2009.
International Preliminary Report on Patentability and Written Opinion of PCT/GB2009/002054 dated Feb. 22, 2011.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,249 dated Jul. 19, 2011.
Office Action in U.S. Appl. No. 11/795,249 dated Oct. 25, 2010.
Office Action in U.S. Appl. No. 11/795,250 dated Dec. 21, 2012.
Office Action in U.S. Appl. No. 11/795,250 dated Mar. 18, 2011.
Office Action in U.S. Appl. No. 11/795,250 dated Jun. 24, 2010.
Office Action in U.S. Appl. No. 11/908,740 dated Feb. 14, 2012.
Office Action in U.S. Appl. No. 11/877,935 dated Dec. 21, 2010.
Office Action in U.S. Appl. No. 12/664,835 dated Feb. 12, 2013.
Office Action in U.S. Appl. No. 13/060,121 dated Jul. 8, 2013.
Office Action in U.S. Appl. No. 11/795,249 dated Dec. 4, 2013.
Office Action in U.S. Appl. No. 11/795,250 dated Dec. 4, 2013.
Office Action in U.S. Appl. No. 12/664,835 dated Oct. 25, 2013.

* cited by examiner

TOPICAL BIOADHESIVE FORMULATIONS

The present invention relates to formulation precursors (pre-formulations) for the in situ generation of controlled release lipid compositions. In particular, the invention relates to pre-formulations in the form of low viscosity mixtures (such as molecular solutions) of amphiphilic components and at least one bioactive agent which undergo at least one phase transition upon exposure to aqueous fluids, such as body fluids, thereby forming a bioadhesive matrix.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable. Furthermore, in some circumstances, such as in the fitting of implants (e.g. joint replacements or oral implants) the area of desired action may not remain accessible for repeated administration. In such cases a single administration must provide active agent at a therapeutic level over the whole period during which activity is needed.

Similarly, where the effect of a bioactive agent is required locally, it may be difficulty or undesirable to administer sufficient of that agent to achieve the effective level throughout the body of the subject. This may be due to undesirable effects of the agent itself (e.g. for steroid anti-inflammatory), or may be because the agent is used to locally counter an undesirable feature of a systemic treatment (such as chemotherapy) but would undermine that primary treatment if used broadly.

A major difficulty with topically applied compositions is, however, their duration of action. These composition are, by their nature, applied to body surfaces which may be prone to abrasion, washing and flushing with bodily or applied fluids, such as tears, sweat or mucous. A particularly difficult situation for the use of topical preparations is in body cavities, such as the GI tract. This is because such cavities are typically coated in a mucous membrane which is non-adherent and turned over rapidly. In addition, thick, viscous preparations can be difficult to apply effectively to the mouth/throat or rectally to the lower GI tract and are difficult to manufacture due to high viscosity preventing sterile filtration. Existing compositions, however, are typically either low viscosity and short-lived or longer lived at the price of high viscosity. Furthermore, existing topical compositions are often capable of containing only a low level of active agent, due to poor compatibility between the base composition and the active agent. This results in a composition which rapidly loses effectiveness as it begins to dissipate from the site of action. It would therefore be of considerable value to provide topical formulations which were bioadherant, even to mucousal surfaces, and which could be formulated as a low viscosity preformulation which would become adherent upon contact with the desired surface. Furthermore it would be a significant advantage if the formulation was protective, non-irritant, and showed reasonable resistance to wear and exposure to aqueous ambient.

The present inventors have now established that by providing a pre-formulation comprising certain amphiphilic components, at least one bioactive agent and a biologically tolerable solvent, especially in a low viscosity phase such as molecular solution, the pre-formulation may be generated addressing many of the shortfalls of previous formulations. In particular, the pre-formulation is easy to manufacture, may be sterile-filtered, it has low viscosity (allowing easy and rapid administration), and/or allows a high level of bioactive agent to be incorporated (thus allowing a smaller amount of composition to be used and/or providing a long effective lifetime). The compositions are formed from materials that are non-toxic, biotolerable and biodegradable. They are suited for application at sensitive areas such as sensitive parts of the body and sites of inflammation, and comprising lipids which are part of natural protective surface linings, e.g. phospholipids. Furthermore, due to the combination of bioadhesive properties and extremely low aqueous solubility of main constituents the compositions, the applied composition of the invention are stable to exposure to aqueous media and wear. The composition furthermore provides sustained release of a wide range of actives with a tuneable window of duration. The pre-formulation is therefore highly suitable for the formation of depot compositions following non-parenteral (e.g. topical) administration to body cavities and/or surfaces of the body or elsewhere and are formed from lipids which may provide inherent benefits in themselves in addition to forming highly effective carriers and topical depots for active agents.

In a first aspect, the present invention thus provides a pre-formulation comprising a low viscosity mixture of:
a) at least one neutral diacyl lipid and/or a tocopherol;
b) at least one phospholipid;
c) at least one biocompatible, (preferably oxygen containing) organic solvent;
including at least one bioactive agent which is dissolved or dispersed in the low viscosity mixture, wherein the pre-formulation forms, or is capable of forming, at least one liquid crystalline phase structure upon contact with an aqueous fluid and/or body surface.

Generally, the aqueous fluid will be a body fluid such as fluid from a mucosal surface, tears, sweat, saliva, gastro-intestinal fluid, extra-vascular fluid, extracellular fluid, interstitial fluid or plasma, and the pre-formulation will form a liquid crystalline phase structure when contacted with a body surface, area or cavity (e.g. in vivo) upon contact with the aqueous body fluid. The pre-formulation of the invention will generally not contain any significant quantity of water prior to administration.

In a second aspect of the invention, there is also provided a method of delivery of a bioactive agent to a human or non-human animal (preferably mammalian) body, this method comprising topically administering a pre-formulation comprising a low viscosity mixture of:
a) at least one neutral diacyl lipid and/or a tocopherol;
b) at least one phospholipid;
c) at least one biocompatible, (preferably oxygen containing) organic solvent;

and including at least one bioactive agent dissolved or dispersed in the low viscosity mixture; whereby to form at least one liquid crystalline phase structure upon contact with an aqueous fluid at a body surface following administration. Preferably, the pre-formulation administered in such a method is a pre-formulation of the invention as described herein.

The method of administration suitable for the above method of the invention will be a method appropriate for the condition to be treated and the bioactive agent used. A bioadhesive non-parenteral (e.g. topical) depot composition may be formed by administration to the surface of skin, mucous membranes and/or nails, to opthalmological, nasal, oral or internal surfaces or to cavities such as nasal, rectal, vaginal or buccal cavities, the periodontal pocket or cavities formed following extraction of a natural or implanted structure or prior to insertion of an implant (e.g a joint, stent, cosmetic implant, tooth, tooth filling or other implant).

In a further aspect, the present invention also provides a method for the preparation of a liquid crystalline composition (especially a depot composition) comprising exposing a pre-formulation comprising a low viscosity mixture of:
a) at least one neutral diacyl lipid and/or a tocopherol;
b) at least one phospholipid;
c) at least one biocompatible (preferably oxygen containing), organic solvent;
and at least one bioactive agent dissolved or dispersed in the low viscosity mixture, to an aqueous fluid at a body surface. Preferably the pre-formulation administered is a pre-formulation of the present invention as described herein. The exposure to a fluid may be internally within at an internal surface of a body cavity, or may be at an external body surface such as a skin surface, depending upon the nature of the composition and any active agent.

The liquid crystalline composition formed in this method is bioadhesive as described herein.

In a still further aspect the present invention provides a process for the formation of a pre-formulation suitable for the administration of a bioactive agent to a surface of a (preferably mammalian) subject, said process comprising forming a low viscosity mixture of
a) at least one neutral diacyl lipid and/or a tocopherol;
b) at least one phospholipid;
c) at least one biocompatible (preferably oxygen containing), organic solvent;
and dissolving or dispersing at least one bioactive agent in the low viscosity mixture, or in at least one of components a, b or c prior to forming the low viscosity mixture. Preferably the pre-formulation so-formed is a formulation of the invention as described herein.

In a yet still further aspect the present invention provides the use of a low viscosity mixture of:
a) at least one neutral diacyl lipid and/or a tocopherol;
b) at least one phospholipid;
c) at least one biocompatible (preferably oxygen containing), organic solvent;
wherein at least one bioactive agent is dissolved or dispersed in the low viscosity mixture in the manufacture of a pre-formulation for use in the sustained local administration of said active agent, wherein said pre-formulation is capable of forming at least one liquid crystalline phase structure upon contact with an aqueous fluid.

In a further aspect, the present invention provides a method for the treatment of a human or animal subject comprising administration of a composition of the present invention, including an active agent. In this aspect, the method of treatment is in particular a method for the treatment of inflammation and/or irritation, especially at a body surface and/or in a body cavity such as the gastrointestinal tract.

In a still further aspect, the present invention provides for the use of a composition of the present invention in therapy, and in particularly for the use of a composition of the present invention, including an active agent, in the manufacture of a medicament for the treatment of inflammation and/or irritation, especially at a body surface and/or in a body cavity such as the gastrointestinal tract.

The use of non-lamellar phase structures (such as liquid crystalline phases) in the delivery of bioactive agents is now relatively well established. Such structures form when an amphiphilic compound is exposed to a solvent because the amphiphile has both polar and apolar groups which cluster to form polar and apolar regions. These regions can effectively solubilise both polar and apolar compounds. In addition, many of the structures formed by amphiphiles in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments, including enzymes, and thereby provide advantageous control over active agent stability and release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and L3 phases are thermodynamically stable systems. That is to say, they are not simply a meta-stable state that will separate and/or reform into layers, lamellar phases or the like, but are the stable thermodynamic form of the lipid/solvent mixture.

As used herein, the term "low viscosity mixture" is used to indicate a mixture which may be readily administered to a subject and in particular readily administered by means of a standard syringe and needle or pump/aerosol spray arrangement. This may be indicated, for example by the ability to be dispensed from a 1 ml disposable syringe through a 22 awg (or a 23 gauge) needle by manual pressure. In a particularly preferred embodiment, the low viscosity mixture should be a mixture capable of passing through a standard sterile filtration membrane such as a 0.22 µm syringe filter. In other preferred embodiments, a similar functional definition of a suitable viscosity can be defined as the viscosity of a pre-formulation that can be sprayed using a compression pump or pressurized spray device using conventional spray equipment. A typical range of suitable viscosities would be, for example, 0.1 to 5000 mPas, preferably 1 to 1000 mPas at 20° C.

Figure 2:
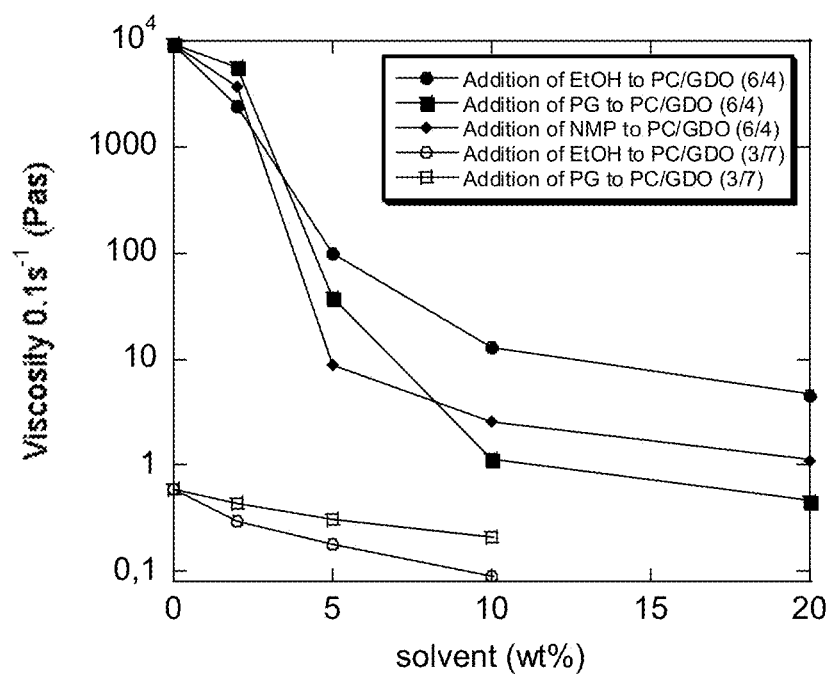

It has been observed that by the addition of small amounts of low viscosity solvent, as indicated herein, a very significant change in viscosity can be provided. As indicated in FIG. 2, for example, the addition of only 5% solvent can reduce viscosity 100-fold and addition of 10% may reduce the viscosity up to 10,000 fold.

In order to achieve this non-linear, synergistic effect, in lowering viscosity it is important that a solvent of appropriately low viscosity and suitable polarity be employed. Such solvents include those described herein infra.

Particularly preferred examples of low viscosity mixtures are molecular solutions and/or isotropic phases such as L2 and/or L3 phases. As describe above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases as described below.

The present invention provides a pre-formulation comprising components a, b, c and at least one bioactive agent as indicated herein. One of the considerable advantages of the pre-formulations of the invention is that components a and b may be formulated in a wide range of proportions. In particular, it is possible to prepare and use pre-formulations of the present invention having a much greater proportion of phospholipid to neutral, diacyl lipid and/or tocopherol than was previously achievable without risking phase separation and/or unacceptably high viscosities in the pre-formulation. The weight ratios of components a:b may thus be anything from 5:95 right up to 95:5. Preferred ratios would generally be from 90:10 to 20:80 and more preferably from 85:15 to 30:70. In one preferred embodiment of the invention, there is a greater proportion of component b than component a. That is, the weight ratio a:b is below 50:50, e.g. 48:52 to 2:98, preferably, 40:60 to 10:90 and more preferably 35:65 to 20:80.

In on preferred embodiment, the compositions are bioadhesive and the ratio of components a:b is in the range 80:20 to 40:60, preferably 70:30 to 50:50. A particularly suitable range is around 65:35 a:b, such as between 75:25 and 55:45.

The amount of component c in the pre-formulations of the invention will be at least sufficient to provide a low viscosity mixture (e.g. a molecular solution, see above) of components a, b and c and will be easily determined for any particular combination of components by standard methods. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases. Viscosity may be measured directly by standard means. As described above, an appropriate practical viscosity is that which can effectively be syringed and particularly sterile filtered and/or sprayed from a pump or pressurised spray. This will be assessed easily as indicated herein. The maximum amount of component c to be included will depend upon the exact application of the pre-formulation but generally the desired properties will be provided by any amount forming a low viscosity mixture (e.g. a molecular solution, see above) and/or a solution with sufficiently low viscosity.

Since the administration of unnecessarily large amounts of solvent to a subject is generally undesirable the amount of component c may, in one embodiment, be limited to no more than ten times (e.g. three times) the minimum amount required to form a low viscosity mixture, preferably no more than five times and most preferably no more than twice this amount.

Higher proportions of solvent may also be used for the non-parenteral (e.g. topical) applications of the invention, however, especially when applied to external body surfaces, where the solvent will be lost by evaporation rather than absorbed into the body. For such applications up to 100 times the minimum amount of solvent may be used (e.g. up to 95% by weight of the composition, preferably up to 80% by weight and more preferably up to 50% by weight), especially where a very thin layer of the resulting non-parenteral depot is desired.

Where the compositions of the invention are formulated as aerosol spray compositions (e.g. for topical or delivery of an active), the composition may also comprise a propellant. Such compositions may also include a high proportion of solvent component c), as considered above, since much of the solvent will evaporate when the composition is dispensed, particularly under the influence of the propellant.

Suitable propellants are volatile compounds which will mix with the composition of the invention under the pressure of the spray dispenser, without generating high viscosity mixtures. They should evidently have acceptable biocompatibility. Suitable propellants will readily be identified by simple testing and examples include hydrocarbons (especially $C_1$ to $C_4$ hydrocarbons), carbon dioxide and nitrogen. Volatile hydrofluorocarbons such as HFCs 134, 134a, 227ea and/or 152a may also be suitable.

As a general guide, the weight of component c will typically be around 0.5 to 50% of the total weight of the a-b-c solution. This proportion may be limited to 2 to 30% or 5 to 20% by weight. As indicated above; however, in case of a spray composition, especially with a propellant, the amount of c may exceed 50%.

The formulations of the invention may additionally contain small proportions of other agent, such as polymers which are soluble in the precursor. Such polymers may act as a reinforcement of the swollen liquid crystalline phase so that a film attached to a mucosal surface is more strongly attached. A "reinforcement" along the same principle could also be obtained by soaking a matrix (paper, polymer net, or similar) with the precursor. Upon applying this "patch" to the skin the formulation may by itself act as the glue. In contrast to conventional adhesives for coating damaged tissue, whoever, the formulations of the invention are adhesive even to mucous membranes and are not irritant. In many cases, they are in fact soothing in themselves, as described herein, and may contain suitable active agent.

Component "a" as indicated herein is a neutral lipid component comprising a polar "head" group and also non-polar "tail" groups. Generally the head and tail portions of the lipid will be joined by an ester moiety but this attachment may be by means of an ether, an amide, a carbon-carbon bond or other attachment. Preferred polar head groups are non-ionic and include polyols such as glycerol, diglycerol and sugar moieties (such as inositol and glucosyl based moieties); and esters of polyols, such as acetate or succinate esters. Preferred polar groups are glycerol and diglycerol, especially glycerol.

In one preferred aspect, component a is a diacyl lipid in that it has two non-polar "tail" groups. This is generally preferable to the use of mono-acyl ("lyso") lipids because these are typically less well tolerated in vivo. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoly (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

The diacyl lipid, when used as all or part of component "a", may be synthetic or may be derived from a purified and/or chemically modified natural sources such as vegetable oils. Mixtures of any number of diacyl lipids may be used as component a. Most preferably this component will include at least a portion of diacyl glycerol (DAG), especially glycerol dioleate (GDO). In one favoured embodiment, component a consists of DAGs. These may be a single DAG or a mixture of DAGs. A highly preferred example is DAG comprising at least 50%, preferably at least 80% and even comprising substantially 100% GDO.

An alternative or additional highly preferred class of compounds for use as all or part of component a are tocopherols. As used herein, the term "a tocopherol" is used to indicate the non-ionic lipid tocopherol, often known as vitamin E, and/or any suitable salts and/or analogues thereof. Suitable analogues will be those providing the phase-behaviour, lack of toxicity, and phase change upon exposure to aqueous fluids, which characterise the compositions of the present invention. Such analogues will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour or lack of toxicity. Typically, a tocopherol will contain no more than 10% of non-tocopherol-analogue compounds, preferably no more than 5% and most preferably no more than 2% by weight.

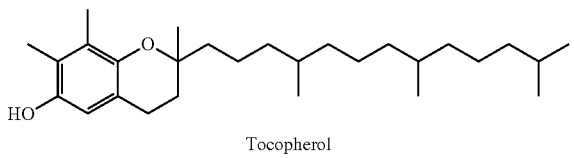 [SMILES: Cc1c(O)cc2c(c1C)OC(C)(CCCC(C)CCCC(C)CCCC(C)C)CC2]
Tocopherol

In a further advantageous embodiment of the invention, component a) consists essentially of tocopherols, in particular tocopherol as shown above.

A preferred combination of constituents for component a) is a mixture of at least one DAG (e.g. GDO) with at least one tocopherol. Such mixtures include 2:98 to 98:2 by weight tocopherol:GDO, e.g. 10:90 to 90:10 tocopherol:GDO and especially 20:80 to 80:20 of these compounds. Similar mixtures of tocopherol with other DAGs are also suitable.

Component "b" in the present invention is at least one phospholipid. As with component a, this component comprises a polar head group and at least one non-polar tail group. The difference between components a and b lies principally in the polar group. The non-polar portions may thus suitably be derived from the fatty acids or corresponding alcohols considered above for component a. It will typically be the case that the phospholipid will contain two non-polar groups, although one or more constituents of this component may have one non-polar moiety. Where more than one non-polar group is present these may be the same or different.

Preferred phospholipid polar "head" groups include phosphatidylcholine, phosphatidylethanolamine, phosphatidylserine and phosphatidylinositol. Most preferred is phosphatidylcholine (PC). In a preferred embodiment, component b) thus consists of at least 50% PC, preferably at least 70% PC and most preferably at least 80% PC. Component b) may consist essentially of PC.

The phospholipid portion, even more suitably than any diacyl lipid portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids.

Since the pre-formulations of the invention may be administered to a subject for the controlled release of an active agent, it is preferable that the components a and b are biocompatible. In this regard, it is preferable to use, for example, diacyl lipids and phospholipids rather than mono-acyl (lyso) compounds. A notable exception to this is tocopherol, as described above. Although having only one alkyl chain, this is not a "lyso" lipid in the convention sense. The nature of tocopherol as a well tolerated essential vitamin evidently makes it highly suitable in biocompatibility.

The nature of the compositions of the invention as being suitable for soothing and healing irritation and inflammation at a body surface makes the need to well tolerated lipids highly important. In particular, the lipid composition will be present at high concentration with tissue which may be damaged or inflamed. As a result, the very high level of compatibility of, for example, the diacyl lipids of the present invention, is significant in comparison with less well tolerated components such as mono-acyl lipids.

It is furthermore most preferable that the lipids and phospholipids of components a and b are naturally occurring (whether they are derived from a natural source or are of synthetic origin). Naturally occurring lipids tend to cause lesser amounts of inflammation and reaction from the body of the subject. Not only is this more comfortable for the subject but it may increase the residence time of the resulting depot composition, since less immune system activity is recruited to the administration site and there is less tendency for the subject to disturb the area. In certain cases it may, however, be desirable to include a portion of a non-naturally-occurring lipid in components a and/or b. This might be, for example an "ether lipid" in which the head and tail groups are joined by an ether bond rather than an ester. Such non-naturally-occurring lipids may be used, for example, to alter the rate of degradation of the resulting depot-composition by having a greater or lesser solubility or vulnerability to breakdown mechanisms present at the site of active agent release. Although all proportions fall within the scope of the present invention, generally, at least 50% of each of components a and b will be naturally occurring lipids. This will preferably be at least 75% and may be up to substantially 100%.

Two particularly preferred combinations of components a and b are GDO with PC and tocopherol with PC, especially in the region 30-90 wt % GDO/tocopherol, 10-60 wt % PC and 1-30% solvent (especially ethanol, NMP and/or isopropanol). Most preferred combinations are 35-60% (e.g. 40-55) GDO with 20 to 50% (e.g. 25 to 45%) PC. These are especially suitable in combination with ethanol, particularly at 5 to 25% (e.g. 7 to 19%).

In addition to amphiphilic components a and b, the pre-formulations of the invention may also contain additional amphiphilic components at relatively low levels. In one embodiment of the invention, the pre-formulation contains up to 10% (by weight of components a and b) of a charged amphiphile, particularly an anionic amphiphile such as a fatty acid. Preferred fatty acids for this purpose include caproic, caprylic, capric, lauric, myristic, palmitic, phytanic, palmitolic, stearic, oleic, elaidic, linoleic, linolenic, arachidonic, behenic or lignoceric acids, or the corresponding alcohols.

Preferable fatty acids are palmitic, stearic, oleic and linoleic acids, particularly oleic acid. It is particularly advantageous that this component be used in combination with a cationic peptide active agent (see below). The combination of an anionic lipid and a cationic peptide is believed to provide a sustained release composition of particular value. This may in part be due to increased protection of the peptide from the degradative enzymes present in vivo.

Component "c" of the pre-formulations of the invention is an oxygen containing organic solvent. Since the pre-formulation is to generate a depot/bioadhesive composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

A special case is where the composition of the invention is formulated as aerosol spray compositions. Here component c may be seen to comprise the propellant, having a low aqueous solubility. All mixing ratios from essentially pure propellant to mainly oxygen containing organic solvents may be considered. When dispensing the formulation the propellant will to a large degree evaporate. When c mainly constitutes propellant an instant increase of viscosity may be observed after spraying the formulation. This is due to rapid evaporation of the propellant and may have the advantage of a more effective initial retention at the application site, and the potential disadvantage that the formulation has a low viscosity during "curing" (uptake of water and phase transformation to a liquid crystalline phase with high viscosity) is circumvented.

In a preferred version, the solvent is such that a relatively small addition to the composition comprising a and b, i.e. below 20%, or more preferably below 16%, e.g. up to 10% or even below give a large viscosity reductions of one order of magnitude or more. As described herein, the addition of 10% solvent can give a reduction of two, three or even four orders of magnitude in viscosity over the solvent-free composition, even if that composition is a solution or $L_2$ phase containing no solvent, or an unsuitable solvent such as water (subject to the special case considered below), or glycerol.

Typical solvents suitable for use as component c include at least one solvent selected from alcohols, ketones, esters (including lactones), ethers, amides and sulphoxides. Examples of suitable alcohols include ethanol, isopropanol and glycerol formal. Monools are preferred to diols and polyols. Where diols or polyols are used, this is preferably in combination with an at least equal amount of monool or other preferred solvent. Examples of ketones include acetone, n-methyl pyrrolidone (NMP), 2-pyrrolidone, and propylene carbonate. Suitable ethers include diethylether, glycofurol, diethylene glycol monoethyl ether, dimethylisobarbide, and polyethylene glycols. Suitable esters include ethyl acetate and isopropyl acetate and dimethyl sulphide is as suitable sulphide solvent. Suitable amides and sulphoxides include dimethylacetamide (DMA) and dimethylsulphoxide (DMSO), respectively. Less preferred solvents include dimethyl isosorbide, tetrahydrofurfuryl alcohol, diglyme and ethyl lactate. The most preferred solvent comprises ethanol and in particular consists of at least 80% ethanol, preferably at least 90% ethanol.

Since the pre-formulations are to be administered to a living subject, it is necessary that the solvent component c is sufficiently biocompatible. The degree of this biocompatibility will depend upon the application method and since component c may be any mixture of solvents, a certain amount of a solvent that would not be acceptable in large quantities may evidently be present. Overall, however, the solvent or mixture forming component c must not provoke unacceptable reactions from the subject upon administration. Generally such solvents will be hydrocarbons or preferably oxygen containing hydrocarbons, both optionally with other substituents such as nitrogen containing groups. It is preferable that little or none of component c contains halogen substituted hydrocarbons since these tend to have lower biocompatibility. Where a portion of halogenated solvent such as dichloromethane or chloroform is necessary, this proportion will generally be minimised. Evidently, the range of suitable solvents will be greater in formulations for application to sound, external surfaces than to internal, sensitive and/or damaged surfaces, where only the most biocompatible will typically be acceptable. In addition, in the case of aerosol spray compositions also halogenated hydrocarbons may be considered as propellant, since it will evaporate to a large degree during dispensing.

Component c as used herein may be a single solvent or a mixture of suitable solvents but will generally be of low viscosity. This is important because one of the key aspects of the present invention is that it provides preformulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

The solvent component c will generally be at least partially lost upon formation of the depot/bioadhesive composition on contact with a surface (e.g. a body surface or the surface of an implant), or diluted by absorption of water from the surrounding air and/or tissue. It is preferable, therefore, that component c be at least to some extent water miscible and/or dispersible and at least should not repel water to the extent that water absorption is prevented. In this respect also, oxygen containing solvents with relatively small numbers of carbon atoms (for example up to 10 carbons, preferably up to 8 carbons) are preferred. Obviously, where more oxygens are present a solvent will tend to remain soluble in water with a larger number of carbon atoms. The carbon to heteroatom (e.g. N, O, preferably oxygen) ratio will thus often be around 1:1 to 6:1, preferably 2:1 to 4:1. Where a solvent with a ratio outside one of these preferred ranges is used then this will preferably be no more than 75%, preferably no more than 50%, in combination with a preferred solvent (such as ethanol). This may be used, for example to decrease the rate of evaporation of the solvent from the pre-formulation in order to control the rate of liquid crystalline depot formation.

A further advantage of the present pre-formulations is that a higher level of bioactive agent may be incorporated into the system. In particular, by appropriate choice of components a-c (especially c), high levels of active agent may be dissolved or suspended in the pre-formulations. Generally, the lipid components in the absence of water are relatively poorly solubilising but in the presence of water form phases too viscous to administer easily. Higher proportions of bioactive agent may be included by use of appropriate solvents as component c and this level will either dissolve in the depot composition as it forms in situ or may form microdrops or microcrystals which will gradually dissolve and release active agent. A suitable choice of solvent will be possible by routine experimentation within the guidelines presented herein. In particular, the present inventors have established that the combination of a low molecular weight alcohol solvent (such as ethanol or isopropanol) with the lipid components of the present invention is unexpectedly effective in solubilising a wide range of drugs and other active molecules.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described.

In some cases the composition may contain a trace of water (or a polar solvent with similar properties) such that it forms a rather low viscous L2 (reversed micellar) phase. This can also help to solubilise certain actives in the formulation, particularly those which are only soluble in water.

There is, however, a certain embodiment of the present invention in which higher proportions of water may be tolerated. This is where water is present as a part of the solvent component in combination with an additional water-miscible component c (single solvent or mixture). In this embodiment, up to 10 wt % water may be present providing that at least 3 wt %, preferably at least 5% and more preferably at least 7 wt % component c is also present, that component c is water miscible, and that the resulting pre-formulation remains non-viscous and thus does not form a liquid crystalline phase. Generally there will be a greater amount of component c) by weight than the weight of water included in the preformulation. Most suitable solvents of use with water in this aspect of the invention include ethanol, isopropyl alcohol, NMP, acetone and ethyl acetate.

The pre-formulations of the present invention contain one or more bioactive agents (described equivalently as "active agents" herein). Active agents may be any compound having a desired biological or physiological effect, such as a protein, drug, antigen, nutrient, cosmetic, fragrance, flavouring, diagnostic, pharmaceutical, vitamin, or dietary agent and will be formulated at a level sufficient to provide an in vivo concentration at a functional level (this generally being a local concentration for topical compositions).

Drug agents that may be delivered by the present invention include drugs which act on cells and receptors, such as peripheral nerves, adrenergic receptors, and cholinergic receptors, the skeletal muscles, the cardiovascular system, smooth muscles, the blood circulation system, endocrine and hormone system, blood circulatory system, synoptic sites, neuroeffector junctional sites, the immunological system, the reproductive system, the skeletal system, autacoid system, the alimentary and excretory systems, the histamine system, and the central nervous system. Drug agents intended for local stimulatory or inhibitory effects on enzymes or proteins can also be delivered by the present invention. The effect of the delivered drug agent may also be associated with direct effects on DNA and/or RNA synthesis, such as on transcription, translation, or post-translational modification. Also these effects may be both stimulatory and inhibitory.

Examples of drugs which may be delivered by the composition of the present invention include, but are not limited to, antibacterial agents such as β-lactams or macrocyclic peptide antibiotics, anti fungal agents such as polyene macrolides (e.g. amphotericin B) or azole antifungals, anti-cancer and/or anti viral drugs such as nucleoside analogues, paclitaxel and derivatives thereof, anti inflammatorys, such as non-steroidal anti inflammatory drugs and corticosteroids, cardiovascular drugs such as blood-pressure lowing or raising agents (especially locally acting), analgesics, and prostaglandins and derivatives. Preferably the drug delivered is a corticosteroid, more preferably a Group A, Group B and/or Group C corticosteroid, with Group A corticosteroids being a preferred example. Diagnostic agents include radionuclide labelled compounds and contrast agents including X-ray, ultrasound and MRI contrast enhancing agents (especially for application to an internal surface of a body cavity). Nutrients include vitamins, coenzymes, dietary supplements etc which may, for example, be used for local rescue from the effects of a systemic drug, such as rescue by folate from a folate analogue such as methotrexate.

Particularly suitable active agents include those which would normally have a short residence time in the body due to rapid breakdown or excretion and those with poor oral bioavailability, especially where their effect may be provided by topical treatment, thereby bypassing systemic absorption. These include peptide, protein and nucleic acid based active agents, hormones and other naturally occurring agents in their native or modified forms. By administering such agents in the form of a bioadhesive depot composition formed from the pre-formulation of the present invention, the agents are provided at a sustained level for an extended length of time in spite of having rapid systemic clearance rates. This offers obvious advantages in terms of stability and patient compliance over dosing multiple times each day for the same period. In one preferred embodiment, the active agent thus has a biological half life (upon entry into the blood stream) of less than 1 day, preferably less than 12 hours and more preferably less than 6 hours. In some cases this may be as low as 1-3 hours or less. Suitable agents are also those with poor oral bioavailability relative to that achieved by injection, for where the active agent also or alternatively has a bioavailability of below 0.1%, especially below 0.05% in oral formulations. Similarly, certain agents would be unsuitable or undesirable when administered sytemically but may be administered locally, particularly to external surfaces.

Peptide and protein based active agents are highly suitable for inclusion in the surface-applied depot compositions of the invention. Such agents may be included for their local effect, or may be applied at a surface for systemic action. Suitable actives for local or systemic effect include human and veterinary drugs selected from the group consisting of adrenocorticotropic hormone (ACTH) and its fragments, angiotensin and its related peptides, antibodies and their fragments, antigens and their fragments, atrial natriuretic peptides, bioadhesive peptides, Bradykinins and their related peptides, calcitonins and their related peptides, cell surface receptor protein fragments, chemotactic peptides, cyclosporins, cytokines, Dynorphins and their related peptides, endorphins and P-lidotropin fragments, enkephalin and their related proteins, enzyme inhibitors, immunostimulating peptides and polyaminoacids, fibronectin fragments and their related peptides, gastrointestinal peptides, gonadotrophin-releasing hormone (GnRH) agonists and antagonist, glucagons like peptides, growth hormone releasing peptides, immunostimulating peptides, insulins and insulin-like growth factors, interleukins, luthenizing hormone releasing hormones (LHRH) and their related peptides, melanocyte stimulating hormones and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, somatostatins and their related peptides, substance P and its related peptides, transforming growth factors (TGF) and their related peptides, tumor necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, interferons (Type I and II), interleukins, leptins, leukaemia inhibitory factors, stem cell factors, transforming growth factors and tumor necrosis factors.

In a preferred embodiment, applicable to all aspects of the invention, the active agent is at least one corticosteroid. For example at least one hydrocortisone type (Group A), acetonide type (Group B), betamethasone type (Group C), or ester type (Group D) corticosteroid. Preferably the active agent is at least one group A and/or at least one group B and/or at least one group C corticosteroid, such as at least one from the group consisting of hydrocortisone, hydrocortisone acetate, cortisone acteate, tixocortol pivalate, prednisolone, methylprednisolone, prednisone, triamcinolone acetonide, triamcinolone alcohol, mometason, amcinonide, budesonide, desonide, fluocinonide, fluocinonide acetonide, halcinonide, betamethasone, betamethasone sodium phosphate, dexamethasone, dexamethasone sodium phosphate, and fluocortolone. Most preferably the active agent is tramcinolone or a salt thereof, such as triamcinolone acetonide or triamcinolone alcohol.

A further considerable advantage of the depot compositions of the present invention is that active agents are released gradually over long periods without the need for repeated dosing. The composition are thus highly suitable for children or people who's lifestyle is incompatible with a reliable or repeated dosing regime. Also for "lifestyle" actives where the inconvenience of repeated dosing might outweigh the benefit of the active.

Cationic peptides are particularly suitable for use where a portion of the pre-formulation comprises an anionic amphiphile such as a fatty acid. In this embodiment, preferred peptides include octreotide, lanreotide, calcitonin, oxytocin, interferon-beta and -gamma, interleukins 4, 5, 7 and 8 and other peptides having an isoelectric point above pH 7, especially above pH 8.

In one preferred aspect of the present invention, the composition of the invention is such that an $I_2$ phase, or a mixed phase including $I_2$ phase is formed upon exposure to aqueous fluids and a polar active agent is included in the composition. Particularly suitable polar active agents include peptide and protein actives, oligo nucleotides, and small water soluble actives, including those listed above. Of particular interest in this aspect are the peptide octreotide and other somatostatin related peptides, interferons alpha and beta, glucagon-like peptides 1 and 2 and their receptor agonists, luprorelin and other GnRH agonist, abarelix and other GnRH antagonists, interferon alpha and beta, zolendronate and ibandronate and other bisphosponates, and polar active chlorhexidine (e.g. chlorhexidine digluconate or chlorhexidine dihydrochloride).

The amount of bioactive agent to be formulated with the pre-formulations of the present invention will depend upon the functional dose and the period during which the depot composition formed upon administration is to provide sustained release. Typically, the dose formulated for a particular agent will be around the equivalent of the normal single dose multiplied by the number times greater the expected duration of action the formulation is to provide. Evidently this amount will need to be tailored to take into account any adverse effects of a large dose at the beginning of treatment and so this will generally be the maximum dose used. The precise amount suitable in any case will readily be determined by suitable experimentation.

The formulations of the present invention may form non-parenteral depots where the active agent is slowly released at a body surface. It is particularly significant that the compositions generated from the preformulations are bioadhesive because this allows local release of the active agent over a sustained period. That is to say that the compositions should coat the surface to which they are applied and/or upon which they form as appropriate and should remain even when this surface is subject to a flow of air or liquid and/or rubbing. It is particularly preferable that the liquid crystalline depot compositions formed should be stable to rinsing with water. For example, a small volume (e.g. 100 µl) of depot precursor may be applied to a body surface and be exposed to a flow of five hundred times its own volume of water per minute for 5 minutes. After this treatment, the composition can be considered bioadhesive if less than 50% of the composition or bioactive agent has been lost. Preferably this level of loss will be matched when water equaling 1000 times and more preferably 10 000 times the volume of the composition is flowed past per minute for five, or preferably 10, minutes.

Another advantageous property of the compositions of the invention is that the film generated following administration may not only act as a depot system. This film may also have the advantage of lowering evaporation of water from damaged areas or areas afflicted by a medical condition (where barrier properties of the skin is reduced). Thus, the compositions may have further advantageous properties in themselves and show additive and/or synergistic advantages in combination with active agents, for instance for the prophylaxis of inflammatory or allergic dermatoses and for the care and restoration of sensitive or stressed skin.

Although the non-parenteral depot compositions of the present invention may absorb some or all of the water needed to form a liquid crystalline phase structure from the biological surfaces with which they are contacted, some additional water may also be absorbed from the surrounding air. In particular, where a thin layer of high surface area is formed then the affinity of the composition for water may be sufficient for it to form a liquid crystalline phase structure by contact with the water in the air. The "aqueous fluid" referred to herein is thus, at least partially, air containing some moisture in this embodiment.

Non-parenteral depot compositions will typically be generated by applying the pre-formulation topically to a body surface (external or within a natural or artificially generated body cavity) and/or to the surface of an implant. This application may be by direct application of liquid such as by spraying, dipping, rinsing, application from a pad or ball roller, intra-cavity injection (e.g to an open cavity with or without the use of a needle), painting, dropping (especially into the eyes), applying in the form of a patch, and similar methods. A highly effective method is aerosol or pump spraying and evidently this requires that the viscosity of the pre-formulation be as low as possible and is thus highly suited to the compositions of the invention. Non-parenteral depots may, however, be used to administer systemic agents e.g. transmucosally or transdermally.

Where the formulation is administered in the form of a patch, this may rely on the "glue" function of the composition. This "glue property" may be beneficial for the tissue contacted by the formulation as the compositions can be soothing and rehydrating, as indicted herein. This is in contrast to previously known patches, where the adhesive is typically inert at best.

Conditions particularly suitable for causative or symptomatic treatment by topical bioadhesive depot compositions of the present invention include skin conditions (such as soreness resulting from any cause including chapping, scratching and skin conditions including eczema and herpes) eye conditions, genital soreness (including that due to genital infection such as genital herpes), infections and conditions for the finger and/or toe nails (such as bacterial or fungal infections of the nails such as onychomycosis or poronychia) and in particular inflammation and/or irritation at any body surface. Two particularly suitable conditions which may be improved by use of the compositions of the invention are oral mucositis and inflammatory bowel disease (e.g. crohn's disease or ulcerative collitus). Topical-type bioadhesive formulations may also be used to administer systemic active agents (e.g. medication), particularly by skin adsorption, oral, transdermal or rectal routes. Travel sickness medication is a preferred example, as is nicotine (e.g. in anti-smoking aids). Where context permits, "topical application" as referred to herein includes systemic agents applied non-parenterally to a specific region of the body.

Periodontal infections are particularly suitable for treatment by the compositions of the present invention. In particular, known compositions for treating periodontal infection are difficult to apply or are generally ineffective. The most widely used periodontal depot composition comprises insertion of a collagen "chip" into the periodontal space, from which an anti-infective agent is released. This chip is difficult to insert and does not form to match the shape and volume of the periodontal space, so that pockets of infection may remain untreated. In contrast to this, the compositions of the present invention, applied as a low viscosity preformulation, can be easily and quickly injected into the periodontal space and will flow to conform exactly to that space and fill the available volume. The compositions then quickly absorb water to form a robust gel which is resistant to aqueous conditions of the mouth. The only known previous attempt at such an injectable periodontal treatment relied on dispersions of relatively high viscosity which were difficult to apply and were subject to undesirable phase separation. All of these drawbacks are now addressed in the compositions of the present invention as described herein. Highly suitable actives for periodontal administration are anti-antibacterial, antibiotic, anti-inflammatory, and local analgesic agents, in particular benzydamine, triamcinolone, tramadol and particularly chlorhexidine.

Non-parenteral depot compositions are also of significant benefit in combination with non-pharmaceutical active agents, such as cosmetic actives, fragrances, essential oils etc. Such non-pharmaceutical depots will maintain the important aspects of bioadhesion and sustained release to provide prolonged cosmetic effects, but may easily be applied by spraying or wiping. This additionally applies to agents which have both cosmetic and medical (especially prophylactic) benefits such as sun-protective agents. Since the topical depot compositions provide robust, water resistant barriers which can solubilise high levels of actives, they are especially suitable for sunscreens and sunblocks in combination with ultra violet light (UV, e.g. UVa, UVb and/or UVc) absorbing and/or scattering agents, particularly where high levels of protection is desirable. The compositions are furthermore highly biocompatible and may act to moisten and soothe the skin during sun exposure. Compositions of the invention containing soothing agents such as aloe *vera* are also highly suitable for soothing and moistening application after exposure to sunlight, or to skin which is dry, inflamed or damaged due to, for example irritation, burning or abrasion.

Active agents particularly suited to non-parenteral (e.g. topical) depot administration, which includes intra oral, buccal, nasal, ophthalmic, dermal, rectal and vaginal delivery routes, include antibacterials such as chlorhexidine, chloramphenicol, triclosan, tetracycline, terbinafine, tobramycin, fusidate sodium, butenafine, metronidazole (the latter particularly for the (e.g. symtomatic) treatment of acne rosacea—adult acne or some vaginal infections), antiviral, including acyclovir, anti infectives such as bibrocathol, ciprofloxacin, levofloxacin, local analgesics such as benzydamine, lidocaine, prilocaine, xylocaine, bupivacaine, analgesics such as tramadol, fentanyl, sufentanyl, morphine, hydromorphone, methadone, oxycodone, codeine, asperine, acetaminophen, NSAIDS such as ibuprofen, flurbiprofen, naproxene, ketoprofen, fenoprofen, diclofenac, etodalac, diflunisal, oxaproxin, piroxicam, piroxicam, indomethansine, sulindac, tolmethin, salysylic acids such as salisylamide and diflunisal, Cox1 or Cox2 inhibitors such as celecoxib, rofecoxib or valdecoxib, corticosteroids such as group A, group B and/or group C corticosteroids (for example at least one from the group consisting of hydrocortisone, hydrocortisone acetate, cortisone acteate, tixocortol pivalate, prednisolone, methylprednisolone, prednisone, triamcinolone acetonide, triamcinolone alcohol, mometason, amcinonide, budesonide, desonide, fluocinonide, fluocinonide acetonide, halcinonide, betamethasone, betamethasone sodium phosphate, dexamethasone, dexamethasone sodium phosphate, and fluocortolone), anticancer and immuno stimulating agents (for instance, metylaminolevulinat hydrocloride, interferon alpha and beta), anticonvulsants (for instance tiagabine topiramate or gabapentin), hormones (such as testosterone, and testosterone undecanoate, medroxyprogesterone, estradiol) growth hormones (like human growth hormone), and growth factors (like granulocyte macrophage colony-stimulating factor), immuno suppressants (cyclosporine, sirolimus, tacrolimus), nicotine and antivirals (e.g. acyclovir), vitamin D3 and derivatives thereof.

Other particularly suitable actives include:
Acetaminophen, Ibuprofen, Propoxyphene, Codeine, Dihydrocodein, Hydrocodone, Oxycodone, Nalbuphine, Meperidine, Leverorphanol, Hydromorphone, Oxymorphone, Alfentanil, Fentanyl and Sefentanil.

Some specific actives found by the inventors to form highly effective depots of the present invention include the following:

For topical bioadhesive, controlled release products for intraoral (including buccal & periodontal) administration;
i. benzydamine (local analgesic, anti inflammatory) or other local analgesic, analgesic, anti inflammatory, anti bacterial, anti fungal or combination thereof. Composition provides sustained effect at intraoral mucosa, in particular damaged, sensitised, infected mucosa e.g. in patients suffering from oral mucositis (induced by e.g. chemo- and radiotherapy). In particular for treatment of oral mucositis.
ii. tramadol (analgesic). Provides a composition with sustained systemic analgesic effect.
iii. chlorhexidine gluconate (antibacterial) for treatment of periodontal and topical infections. Particularly for long acting effect in periodontal pocket. Compositions result in depots releasing chlorhexidine over more than 1 h, preferably more than 6 h, most preferably more than 24 h when applied as a liquid, forming a bioadhesive gel in situ. Surface gel formation time observed to be between 1 second and 5 min.

Depots i to iii formable having high level of active agent incorporation and high degree of resistance to washing away. Preformulations in the form of a liquid administered as spray or liquid wash/rinse for i and ii and gel-forming liquid for iii, wherein liquid is applied to periodontal pocket, e.g. by injection.

For non-parenteral (e.g. topical or systemic) bioadhesive, controlled release products for nasal administration;
i. fentanyl (analgesic) provides rapid onset and sustained duration analgesia when administered as spray to the nasal or oral cavity
ii. diazepam (anti anxiety) provides non-parenteral, nasal or oral cavity depot with systemic effect giving rapid onset and sustained duration. Administered as a spray For topical bioadhesive, controlled release products for ophthalmic administration;
i. diclofenac (NSAID) with sustained duration. Administered as in situ phase forming liquid
ii. pilocarpine (parasymptomimetic, cholinergic agonist) for treatment of glaucoma.
iii levocabastine hydrochloride, ketotifen fumarate providing liquid for eye-dropping to give long lasting relief from allergic conjunctivitis with long period between reapplication.
iv Pilocarpine hydrochloride for the treatment of Sjögrens syndrome.
v dexamethasone, (corticosteroid)
vi chloramphenicol (primarily bacteriostatic antiinfective)
vii indomethacin (NSAID)

Depots i to vii formulated as liquid spray or more preferably drops for direct application to eye surface and provide in situ depot formation with high resistance to washing out by tears and wear from blinking/eye rubbing. Composition of the invention show excellent compatibility ophthalmic application. Safety studies in rabbit models show no irritation and no blurring effects.

Other actives suitable for ophthalmic compositions include Antihistamines, Mast cell stabilizers, Nonsteroidal anti-inflammatory drugs (NSAIDs), Corticosteroids (e.g. to treat allergic conjunctivitis) such as group A, group B and/or group C corticosteroids (for example at least one from the group consisting of hydrocortisone, hydrocortisone acetate, cortisone acteate, tixocortol pivalate, prednisolone, methylprednisolone, prednisone, triamcinolone acetonide, triamcinolone alcohol, mometason, amcinonide, budesonide, desonide, fluocinonide, fluocinonide acetonide, halcinonide, betamethasone, betamethasone sodium phosphate, dexamethasone, dexamethasone sodium phosphate, and fluocortolone), Anti-Glaucoma actives including inflow suppressing/inhibiting agents (beta blocking agents: timolol, betaxolol, carteolol, levobunolol, etc., topical carbonic anhydrase inhibitors: dorzolamide, brinzolamide, sympathomimetics: epinephrine, dipivefrin, clonidine, apraclonidine, brimonidine), outflow facilitating agents (parasympathomimetics (cholinergic agonists): pilocarpine prostaglandin analogues and related compounds: atanoprost, travoprost, bimatoprost, unoprostone)

For non-parenteral (e.g. topical or systemic) bioadhesive, controlled release products for dermatological administration;
i. acyclovir (antiviral). Composition generates a bioadhesive, film forming product with sustained duration. Applied as spray or liquid
ii. testosterone undecanoate or testosterone enantate (hormone deficiency). Bioadhesive, film forming composition with sustained duration. May be applied as aerosol- or pump-spray, or as liquid.

Particularly suitable applications of dermatological formulations are anti-infective dermatological bioadhesive depots for protection in environments where contact with infective agents is likely (e.g. human or veterinary surgery, abattoir work, certain types of cleaning etc.). Bioadhesive depots generated from composition of the invention provide robust and sustained protection for the wearer. The compositions with antiinfective agents may also be used in situations where skin sterility of the wearer is important for the health of others, such as for nurses or doctors visiting multiple patients in hospital, where cross-infection must be avoided. A prior coating with a composition of the present invention may serve to provide resistance against picking up of infectives from one area and thus prevent transmission to another.

In the methods of treatment of the present invention, as well as in the corresponding use in therapy and the manufacture of medicaments, an active agent is not always necessary. In particular, lipids, particularly phospholipids such as PC have been implicated as highly beneficial in themselves for the treatment of certain conditions (including those described herein below). Without being bound by theory, it is believed that suitable lipids, such as those in the formulations of the present invention, are naturally present in the protective layers over and around many structures of the body, such as the linings of many body cavities and the contact surfaces of joints. These layers may serve as protection from adhesion and attack by a wide variety of chemical and biological agents (such as on gastric surfaces and in the lining of the GI tract), may act as lubricants (particularly in joints but crucially also on the linings and membranes surrounding many internal structures such as heart and lungs), and may additionally contribute to cell wall repair by allowing lipid exchange and dilution of undesirable membrane-bound and membrane-soluble agents. The lipid nature of the compositions also forms a harmless substrate for unwanted inflammatory lipase enzymes including phospholipases such as phospholipase $A_2$ ($PLA_2$).

In an alternative embodiment of the methods of treatment and corresponding uses of the present invention, suitable actives may be included, either as the sole beneficial agent, or to complement the effect of suitable lipid components. Such actives will typically be suited for the treatment of inflammation and/or irritation, such as steroidal and non-steroidal anti-inflammatory drugs and local immune modulators. Examples of such agents are well known and many are mentioned herein elsewhere. They include, cis-urocanic acid, corticosteroids such as prednisone methylprednisolone and hydrocortisone, and derivatives of nonsteroidal anti-inflammatory compounds such as benzydamine, paracetamol, ibuprofen and salicylic acid derivatives including acetyl salicylate and 5-amino salicylates. Local inhibitors of inflammatory pathways are also suitable, including the antigen recognition suppressors methotrexate, azathioprine or 6-mercaptopurine and phospholipase inhibitors, such as $PLA_2$ inhibitors.

The pre-formulations of the present invention provide non-lamellar liquid crystalline depot compositions upon exposure to aqueous fluids, especially in contact with body surfaces. As used herein, the term "non-lamellar" is used to indicate a normal or reversed liquid crystalline phase (such as a cubic or hexagonal phase) or the L3 phase or any combination thereof. The term liquid crystalline indicates all hexagonal liquid crystalline phases, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. By use of the pre-formulations of the present invention it is possible to generate any phase structure present in the phase-diagram of components a and b with water. This is because the pre-formulations can be generated with a wider range of relative component concentrations than previous lipid depot systems without risking phase separation or resulting in highly viscous solutions for injection. In particular, the present invention provides for the use of phospholipid concentrations above 50% relative to the total amphiphile content. This allows access to phases only seen at high phospholipid concentrations, particularly the hexagonal liquid crystalline phases.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ phase are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives.

In transient stages after contact with body fluid the composition can comprise multiple phases since the formation of an initial surface phase will retard the passage of solvent into the core of the depot. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_{II}$ or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase.

It is important to appreciate that the preformulations of the present invention are of low viscosity. As a result, these preformulations must not be in any bulk liquid crystalline phase since all liquid crystalline phases have a viscosity significantly higher than could be administered by syringe or spray dispenser. The preformulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing around 10 wt % or greater of solvent (component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

In one embodiment, a small proportion (e.g. less than 5% by weight) of a reinforcing polymer may be added to the formulation.

Upon administration, the pre-formulations of the present invention undergo a phase structure transition from a low viscosity mixture to a high viscosity (tissue adherent) depot composition. Generally this will be a transition from a molecular mixture, swollen $L_2$ and/or L3 phase to one or more (high viscosity) liquid crystalline phases such as normal or reversed hexagonal or cubic liquid crystalline phases or mixtures thereof. As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes of less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse, releasing the active agent, or may subsequently convert to a cubic liquid crystalline phase, which in turn then gradually disperses. It is believed that the hexagonal phase will provide a more rapid release of active agent, in particular of hydrophilic active agent, than the cubic phase structure, especially the $I_2$ and $L_2$ phase. Thus, where the hexagonal phase forms prior to the cubic phase, this will result in an initial release of active agent to bring the concentration up to an effective level rapidly, followed by the gradual release of a "maintenance dose" as the cubic phase degrades. In this way, the release profile may be controlled.

Without being bound by theory, it is believed that upon exposure (e.g. to body fluids), the pre-formulations of the invention lose some or all of the organic solvent included therein (e.g. by diffusion and/or evaporation) and take in aqueous fluid from the bodily environment (e.g. moist air close to the body or the in vivo environment) such that at least a part of the formulation generates a non-lamellar, particularly liquid crystalline phase structure. In most cases these non-lamellar structures are highly viscous and are not easily dissolved or dispersed into the in vivo environment and are bioadhesive and thus not easily rinsed or washed away. Furthermore, because the non-lamellar structure has large polar, apolar and boundary regions, it is highly effective in solubilising and stabilising many types of active agents and protecting these from degradation mechanisms. As the depot composition formed from the pre-formulation gradually degrades over a period of hours or days, or even weeks or months (depending upon the nature and site of application), the active agent is gradually released and/or diffuses out from the composition. Since the environment within the depot composition is relatively protected, the pre-formulations of the invention are highly suitable for active agents with a relatively low biological half-life (see above).

In an additional aspect of the invention, the topical compositions may be used to provide a physical barrier on body surfaces, in the absence of any active agent. In particular, because of the very high bioadherance of the compositions, "barrier" coatings formed by spraying or application of liquid may be formed from the present compositions so as to reduce contact with potential infective or irritant agents or to reduce soiling of the body surfaces. The robust nature of the compositions and resistance to washing provide advantageous characteristics for such barriers, which could conveniently be applied as a liquid or by spraying. Without being bound to theory it is believed that the stability and wear resistance of applied topical compositions is due to the particular phase transitions of the composition on exposure to aqueous fluid/moisture and the bioadhesion thereof, in combination with the low aqueous solubility of the diacyl lipid building blocks.

The formulations, compositions and methods of the invention relating to the treatment of inflammation or irritation, are particularly suitable for addressing inflammation and/or irritation in a body cavity. Administration to a body cavity is thus highly suitable in this aspect and will be carried out by a method suitable for the cavity being treated. Mouthwashes, for example, may be suitable for oral or buccal cavities, while other parts of the GI tract may be suitably treated by oral formulations, including dispersions and dry pre-formulations, and rectal formulations such as enemas or suppositories. Rinses and pesseries are similarly suitable for vaginal delivery.

The compositions of the present invention are highly suitable for treating inflammation in a body cavity because of the highly bioadhesive nature of the non-lamellar phase and the resulting long-lasting effects. The inherently soothing and highly biocompatible nature of the constituents is also important and may pay a passive or active role in the treatment of inflammation.

The methods of treatment and corresponding uses of the present invention are thus most applicable to inflammatory diseases and inflammation caused by, for example, wounding, abrasion, or reaction to aggressive therapies such as irradiation and/or chemotherapy. Especially suitable are inflammatory diseases affecting at least one body cavity. Diseases of the GI tract are highly suitable for treatment with the compositions of the present invention, particularly inflammatory bowel disease including Crohn's disease and ulcerative collitus and oral inflammation such as oral mucositis. Similarly, application to a body cavity during surgery may also be used to take advantage of the properties of the formulations. They may thus be directly applied, for example by spraying or painting, to sooth inflammation resulting from or exposed during surgery and also to reduce the tendency of surgically manipulated tissue to "stick" and/or form adhesions/bridges at unwanted sites.

The invention thus particularly provides for a method of treatment of an inflammatory disease (e.g. Crohn's disease, ulcerative collitus or oral mucositis), said method comprising the administration of a preformulation of the present invention either in the absence of an active agent, or comprising at least one anti-inflammatory or anti-infective active agent such as one selected from corticosteroids such as prednisone methylprednisolone and hydrocortisone, and derivatives of nonsteroidal anti-inflammatory compounds such as benzydamine, paracetamol, ibuprofen and salicylic acid derivatives including acetyl salicylate and 5-amino salicylates. Local inhibitors of inflammatory pathways are also suitable, including the antigen recognition suppressors methotrexate, azathioprine or 6-mercaptopurine and phospholipase inhibitors, such as $PLA_2$ inhibitors. Other suitable actives include glutamine, antioxidants such as ascorbate, beta-carrotine, vitamin E, oxypentifylline, Azelastine hydrochloride, allopurinol, chlorhexadine, povidone iodine, nystatin, clotrimazole, polymixin E, tobramycin, amphotericin B, acyclovir, granulocyte colony stimulating factor (G-CSF), granulocyte-macrophage stimulating factor (GM-CSF), cytokines and cytokine inducers/supressors.

Preferably the active agent is selected from corticosteroids, preferably group A and/or group B corticosteroids, such as at least one from the group consisting of hydrocortisone, hydrocortisone acetate, cortisone acteate, tixocortol pivalate, prednisolone, methylprednisolone, prednisone, triamcinolone acetonide, triamcinolone alcohol, mometason, amcinonide, budesonide, desonide, fluocinonide, fluocinonide acetonide and halcinonide.

A particularly preferred method and corresponding use is a method for the treatment of oral mucositis in a human or animal subject (especially one in need thereof) by a composition of the present invention (especially comprising preferred combinations of components a), b) and c)) comprising at least one local analgesics or anti-inflammatory agent, especially benzydamine or a derivative thereof. Optionally these may be combined with one or more of the actives indicated above for the treatment of inflammation, and/or with a topical anaesthetic such as lignocaine, cocaine, diphendramine, or particularly dyclonine HCl.

Figure 3:
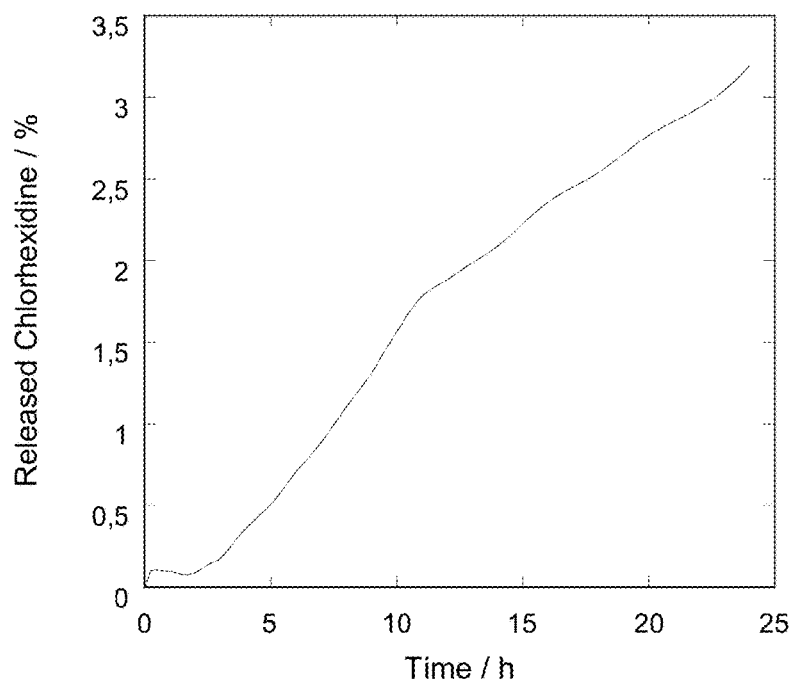

The Invention will now be further illustrated by reference to the following non-limiting Examples and the attached Figures, in which;

FIG. 1 shows the cumulative release of methylene blue (MB) from a depot formulation comprising PC/GDO/EtOH (45/45/10 wt %) when injected into excess water;

FIG. 2 demonstrates the non-linear decrease of pre-formulation viscosity of the depot precursor upon addition of N-methyl pyrrolidinone (NMP) and EtOH;

FIG. 3 displays the in vitro release in excess aqueous phase of chlorhexidine from a depot formulation comprising PC/GDO/EtOH (36/54/10 wt %) containing 50 mg chlorhexidine/g of formulation, corresponding to 5% drug load.

Figure 4:
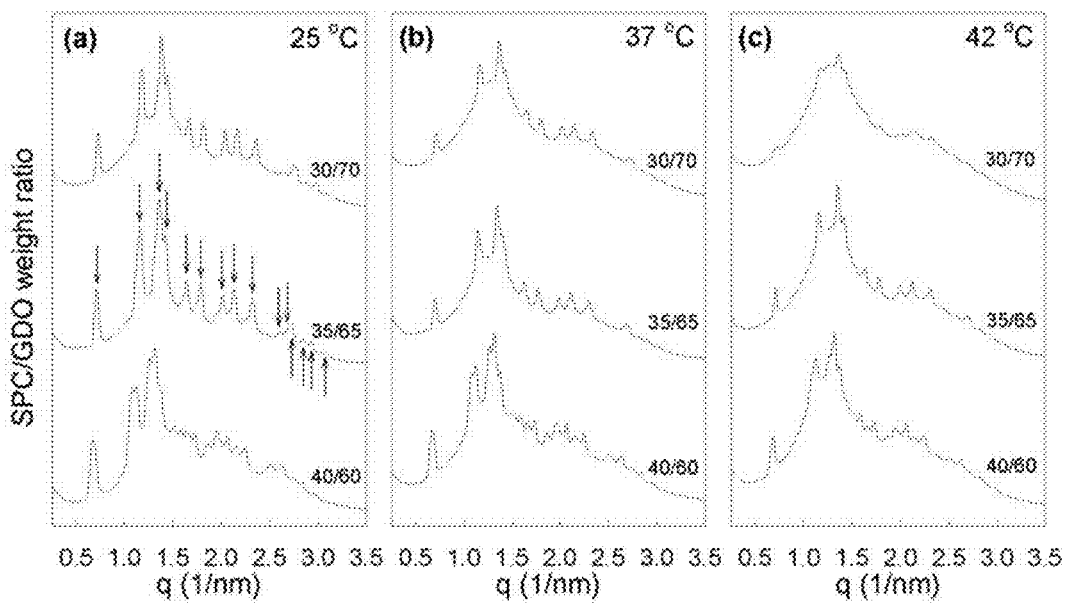

FIG. 4. SAXD profiles of SPC/GDO mixtures in excess PBS as a function of lipid weight ratio at 25 (a), 37 (b), and 42° C. (c) prepared at lipid formulation:PBS weight ratio of 1:2. Arrows in (a) show indexing of the reflections from the reversed micellar Fd3m cubic phase. Explanation is given in the text.

Figure 5:
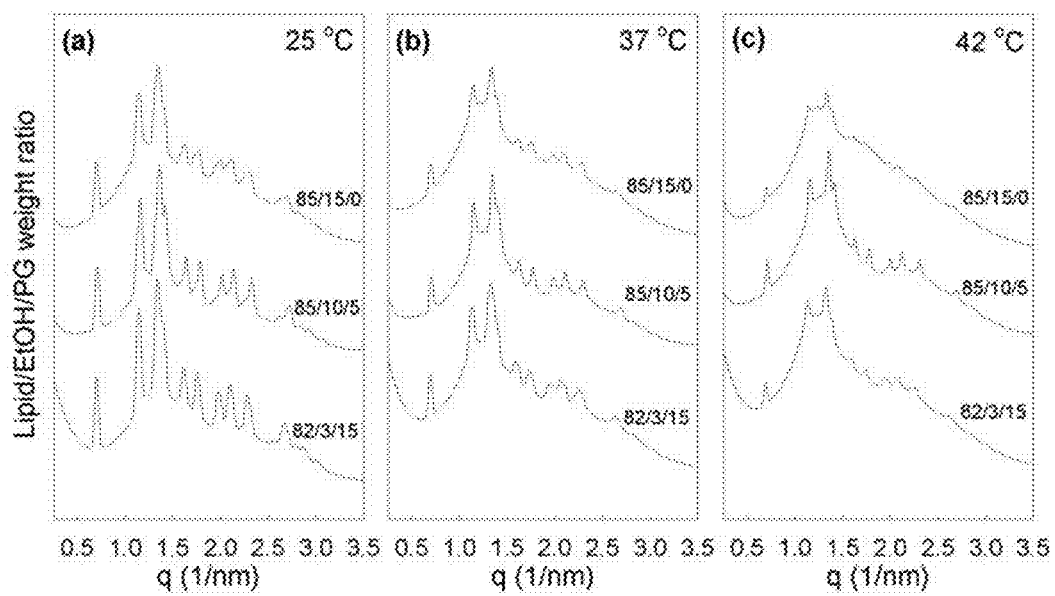

FIG. 5. SAXD profiles of SPC/GDO/EtOH/PG formulations in excess PBS as a function of EtOH/PG weight ratio at 25 (a), 37 (b), and 42° C. (c) prepared at lipid formulation:PBS weight ratio of 1:2. SPC/GDO weight ratio is 35/65 for all samples.

Figure 6:
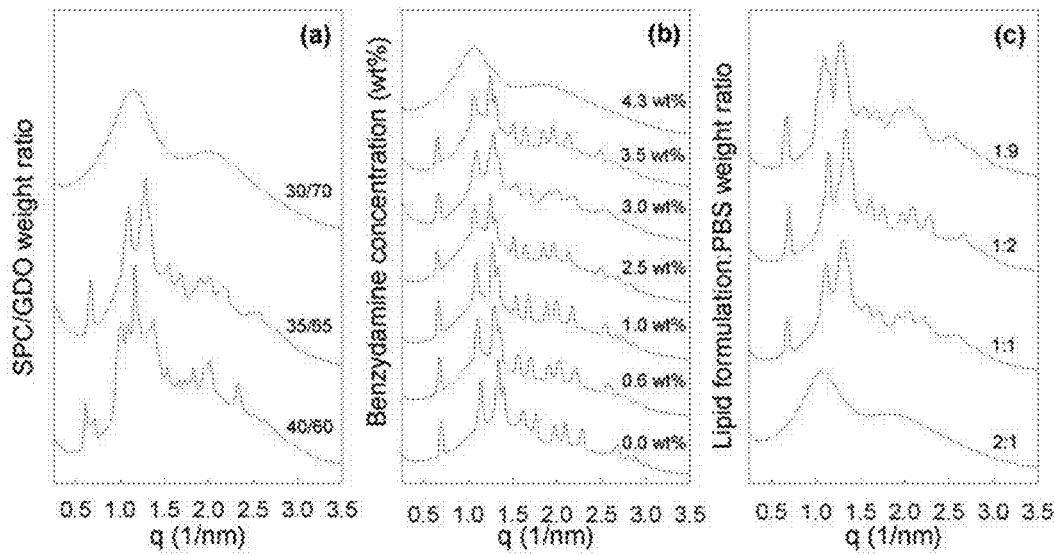

FIG. 6. Effect of 3 wt % of BZD on the liquid crystalline nanostructure as a function of SPC/GDO weight ratio at lipid formulation:PBS weight ratio of 1:2 (a). Effect of BZD concentration on the nanostructure of SPC/GDO liquid crystalline phases prepared at weight ratio of 35/65 (b). Effect of 3 wt % of BZD on the liquid crystalline nanostructure as a function of lipid formulation:PBS weight ratio at SPC/GDO weight ratio weight ratio of 35/65 (c). The lipid/EtOH/PG weight ratio was 85/10/5 for all samples.

Figure 7:
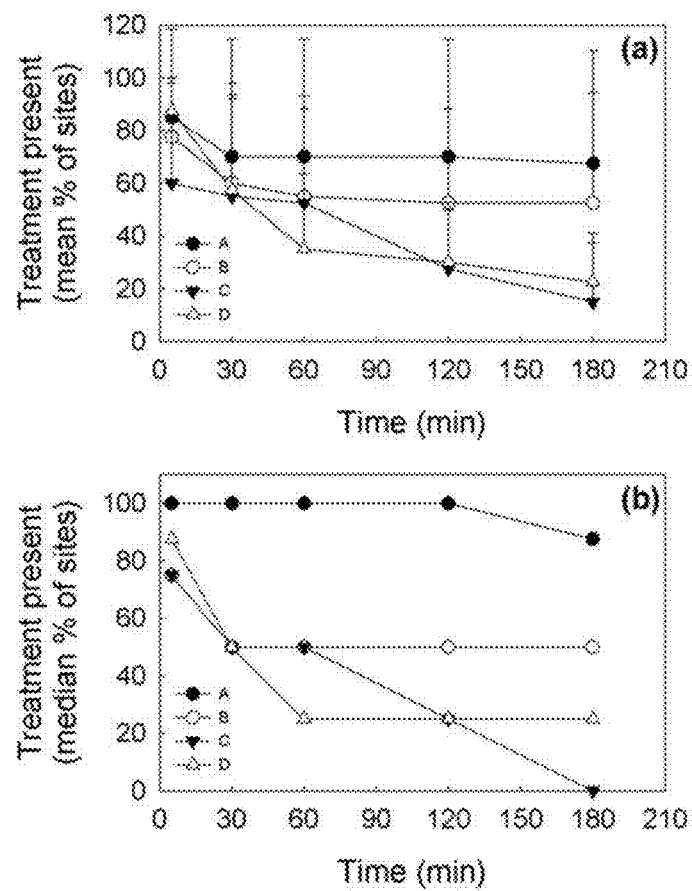

FIG. 7. Time dependence of the mean (±SD) (a) and median (b) values of percentage of sites where treatment was present after administration of SPC/GDO/BZD/EtOH/PG formulations prepared at weight ratios of 53.3/28.7/3/10/5 (A), 53.3/28.7/3/15/0 (B), 57.4/24.6/3/10/5 (C), and 49.2/32.8/3/10/5 (D). Number of examined sites in mouth=8 (left and right sides of the upper palate, lower palate, inside of the cheek and tongue), number of patients=5.

Figure 8:
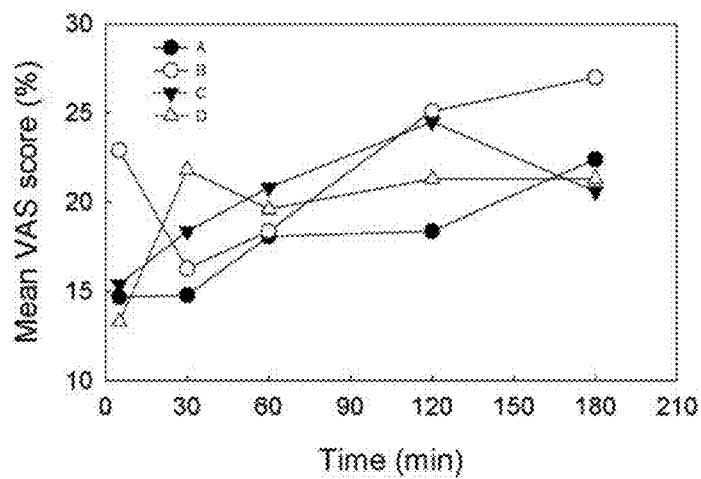

FIG. 8. Time dependence of the mean VAS score after administration of lipid formulation. Patient question form: evaluation of the analgesic effect (pain in mouth). Visual analog scale (VAS): 0=no pain, 100=worst imaginable pain. SPC/GDO/BZD/EtOH/PG formulation compositions by weight are: 53.3/28.7/3/10/5 (A), 53.3/28.7/3/15/0 (B), 57.4/24.6/3/10/5 (C), and 49.2/32.8/3/10/5 (D). Number of patients=5.

Figure 9:
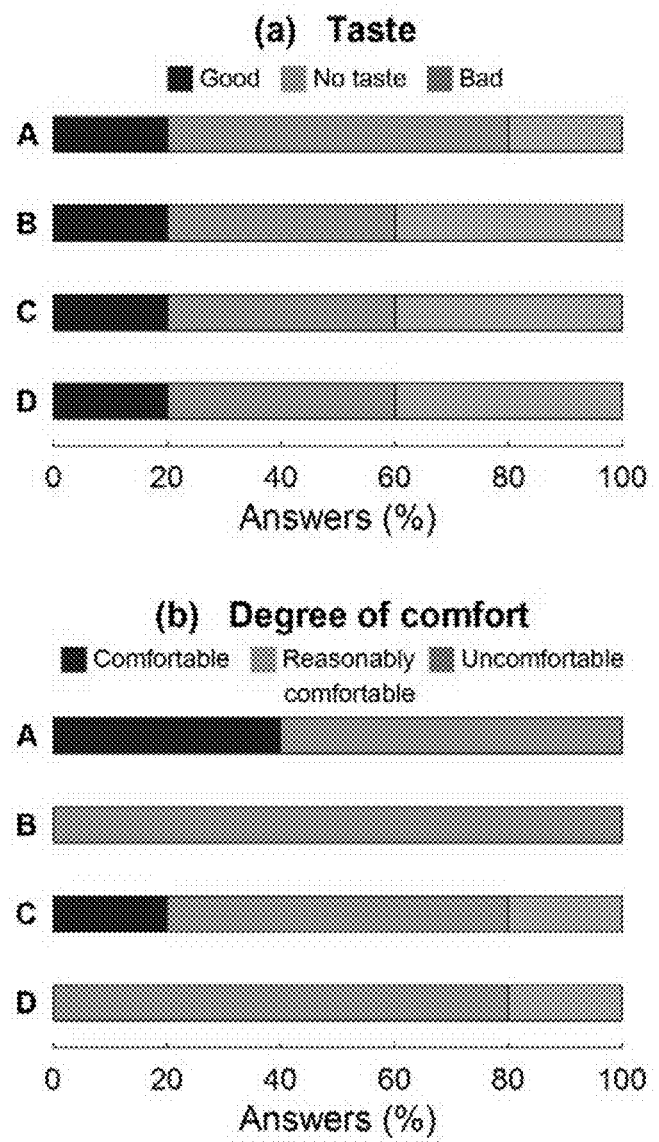

FIG. 9. Patient reported outcomes regarding taste (a) degree of comfort (b) after dosing of lipid formulations to head and neck cancer patients. Formulation compositions by weight are: 53.3/28.7/3/10/5 (A), 53.3/28.7/3/15/0 (B), 57.4/24.6/3/10/5 (C), and 49.2/32.8/3/10/5 (D). Number of patients=5.

Figure 10:
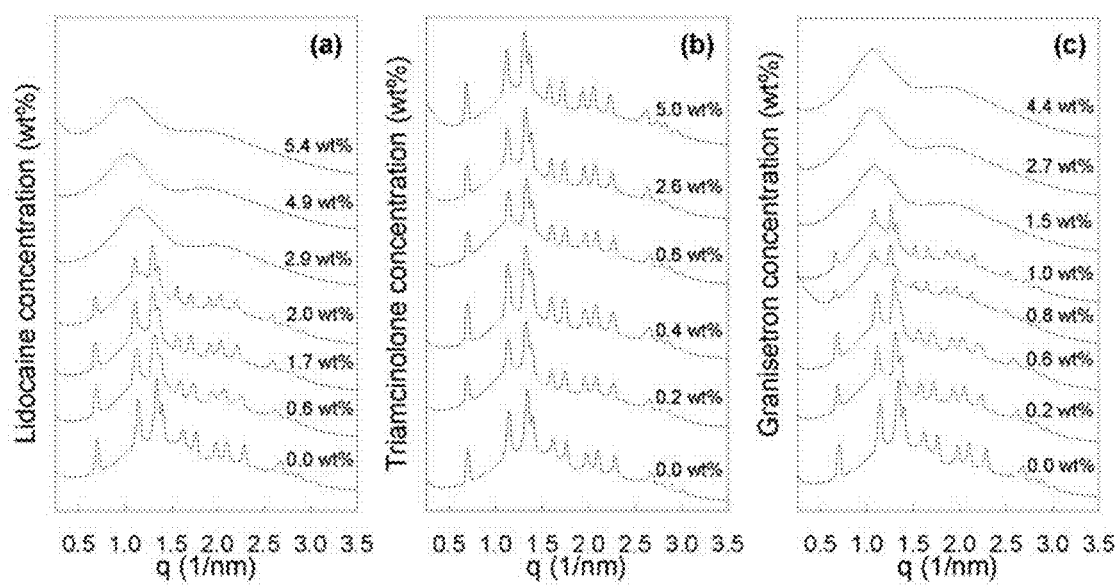

FIG. 10. Effect of lidocaine (a), triamcinolone (b), and graniestron (c) on the nanostructure of SPC/GDO/EtOH/PG liquid crystalline phases. The formulation:PBS weight ratio was 1:2, the SPC/GDO weight ratio was 35/65 and lipid/EtOH/PG weight ratio was 85/10/5 for all samples. The concentration of API is expressed as wt % of the total formulation weight.

EXAMPLES

Example 1

Availability of Various Liquid Crystalline Phases in the Depot by Choice of Composition Injectable formulations containing different proportions of phosphatidyl choline ("PC"—Epikuron 200) and glycerol dioleate (GDO) and with EtOH as solvent were prepared to illustrate that various liquid crystalline phases can be accessed after equilibrating the depot precursor formulation with excess water.

Appropriate amounts of PC and EtOH were weighed in glass vials and the mixture was placed on a shaker until the PC completely dissolved to form a clear liquid solution. GDO was then added to form an injectable homogenous solution.

Each formulation was injected in a vial and equilibrated with excess water. The phase behaviour was evaluated visually and between crossed polarizes at 25° C. Results are presented in Table 1.

TABLE 1

| Formulation | PC (wt %) | GDO (wt %) | EtOH (wt %) | Phase in $H_2O$ |
|---|---|---|---|---|
| A | 22.5 | 67.5 | 10.0 | $L_2$ |
| B | 28.8 | 61.2 | 10.0 | $I_2$ |
| C | 45.0 | 45.0 | 10.0 | $H_{II}$ |
| D | 63.0 | 27.0 | 10.0 | $H_{II}/L_\alpha$ |

$L_2$ = reversed micellar phase
$I_2$ = reversed cubic liquid crystalline phase
$H_{II}$ = reversed hexagonal liquid crystalline phase
$L_\alpha$ = lamellar phase

Example 2

In Vitro Release of a Water-Soluble Substance

A water-soluble colorant, methylene blue (MB) was dispersed in formulation C (see Example 1) to a concentration of 11 mg/g formulation. When 0.5 g of the formulation was injected in 100 ml water a stiff reversed hexagonal $H_{II}$ phase was formed. The absorbancy of MB released to the aqueous phase was followed at 664 nm over a period of 10 days. The release study was performed in an Erlenmeyer flask at 37° C. and with low magnetic stirring.

The release profile of MB (see FIG. 1) from the hexagonal phase indicates that this (and similar) formulations are promising depot systems. Furthermore, the formulation seems to give a low initial burst, and the release profile indicates that the substance can be released for several weeks; only about 50% of MB is released after 10 days.

Example 3

Viscosity in PC/GDO (6:4) or PC/GDO (3:7) on Addition of Solvent (EtOH, PG and NMP)

A mixture of PC/GDO/EtOH was manufactured according to the method in Example 1. All, or nearly all, of the EtOH was removed from the mixture with a rotary evaporator (vacuum, 40° C., 1 h) and the resulting solid mixture were weighed in glass vial after which 2, 5, 10 or 20% of a solvent (EtOH, propylene glycol (PG) or n-methyl pyrrolidone (NMP)) was added. The samples were allowed to equilibrate several days before the viscosity was measured at a shear rate of 0.1 s$^{-1}$ with a Physica UDS 200 rheometer at 25° C.

This example clearly illustrates the need for solvent with certain depot precursors in order to obtain an injectable formulation (see FIG. 2). The viscosity of solvent-free PC/GDO mixtures increases with increasing ratio of PC. Systems with low PC/GDO ratio (more GDO) are injectable with a lower concentration of solvent.

Example 4

Composition and In Vitro Phase Study

The formulations were manufactured according to the method described in Example 1 with compositions according to Table 2. An active substance (peptide), salmon calcitonin (sCT), was added to each formulation to a concentration of 500 μg sCT/g formulation. The formulations were designed as homogenous suspensions for parenteral administration (mixing required shortly prior to use since the drug is not completely dissolved in the PC/GDO/EtOH system).

The phase study in this example is performed in excess of rat serum at 37° C. in order to simulate an in vivo situation. Table 2 shows that the same phases as those in water are formed (compare Table 1).

TABLE 2

| Formulation | PC (wt %) | GDO (wt %) | OA (wt %) | EtOH (wt %) | Phase in rat serum |
|---|---|---|---|---|---|
| E | 18 | 72 | — | 10 | $L_2$ |
| F | 36 | 54 | — | 10 | $I_2$ |
| G | 34 | 51 | 5 | 10 | $I_2$ |
| H | 54 | 36 | — | 10 | $H_{II}$ |
| I | 72 | 18 | — | 10 | $H_{II}/L_\alpha$ |

OA = Oleic Acid

Example 5

Sterile Filtration of Formulations with Reduced Viscosity

To lower the viscosity with various solvents is sometimes necessary in order to obtain an injectable formulation and to be able to administrate the system with a regular syringe (see Example 3). Another important effect from the viscosity-lowering solvent is that the formulations can be sterile filtrated.

Formulations E to I in Example 4 were studied in a sterile filtration test by using a 0.22 nm filter (before addition of the active substance). Formulations E to H were successfully filtrated, but formulation I failed since the viscosity was too high. An aseptic manufacturing procedure was therefore needed for this formulation.

Example 6

Preparation of Depot Precursor Compositions with Various Solvents

Depending on composition of the formulation and the nature and concentration of active substance certain solvents may be preferable.

Depot precursor formulations (PC/GDO/solvent (36/54/10)) were prepared by with various solvents; NMP, PG, PEG400, glycerol/EtOH (90/10) by the method of Example 1. All depot precursor compositions were homogeneous one phase solutions with a viscosity that enabled injection through a syringe (23G—i.e. 23 gauge needle; 0.6 mm×30 mm) After injecting formulation precursors into excess water a liquid crystalline phase in the form of a high viscous monolith rapidly formed with NMP and PG containing precursors. The liquid crystalline phase had a reversed cubic micellar ($I_2$) structure. With PEG400, glycerol/EtOH (90/10) the viscosification/solidification process was much slower and initially the liquid precursor transformed to a soft somewhat sticky piece. The difference in appearance probably reflects the slower dissolution of PEG400 and glycerol towards the excess aqueous phase as compared to that of EtOH, NMP and PG.

Example 7

Preparation of Depot Composition Containing Benzydamine

Benzydamine is a non-steroidal antiinflammatory drug and is extensively used as a topical drug in inflammatory conditions.

1 g of a depot formulation containing 1.5 mg benzydamine was prepared by dissolving the active substance in a mixture of PC/GDO/EtOH (36/54/10) prepared as described in Example 1. The depot composition was stable against crystallization during storage at 25° C. for at least two weeks. Equilibration of the formulation precursor with excess water resulted in a high viscous monolithic liquid crystalline phase ($I_2$ structure).

Example 8

Robustness of the Behaviour of the Formulation Against Variations in the Excipient Quality Depot precursor formulations were prepared with several different GDO qualities (supplied by Danisco, Dk), Table 3, using the method of Example 1. The final depot precursors contained 36% wt PC, 54% wt GDO, and 10% wt EtOH. The appearance of the depot precursors was insensitive to variation in the quality used, and after contact with excess water a monolith was formed with a reversed micellar cubic phase behaviour ($I_2$ structure).

TABLE 3

Tested qualities of GDO.

| GDO quality | Monoglyceride (% wt) | Diglyceride (% wt) | Triglyceride (% wt) |
|---|---|---|---|
| A | 10.9 | 87.5 | 1.6 |
| B | 4.8 | 93.6 | 1.6 |
| C | 1.0 | 97.3 | 1.7 |
| D | 10.1 | 80.8 | 10.1 |
| E | 2.9 | 88.9 | 8.2 |
| F | 0.9 | 89.0 | 10.1 |

Example 9

Preparation of Depot Composition Containing Saturated PC (Epikuron 200SH)

Depot precursor formulations were prepared with various amounts PC comprising saturated hydrocarbon chains by addition of Epikuron 200SH directly to a mixture of PC/GDO/EtOH, prepared as for Example 1. The formulations are shown in Table 4. All precursor formulations were homogenous one phase samples in RT, while they became more viscous with increasing amount Epikuron 200SH. Injecting the depot precursor into excess water gave a monolith comprising a reversed miceller cubic ($I_2$) structure. Monoliths formed from samples containing higher amounts of Epikuron 200SH became turbid, possibly indicating segregation between Epikuron 200SH and the other components upon exposure to water and formation of the 12 phase.

TABLE 4

Depot composition containing saturated PC

| Formulation | Saturated PC, Epikuron 200SH (% wt) | PC (% wt) | GDO (% wt) | EtOH (% wt) |
|---|---|---|---|---|
| G1 | 3.9 | 34.6 | 51.9 | 9.6 |
| G2 | 7.0 | 33.5 | 50.2 | 9.3 |
| G3 | 14.3 | 30.8 | 46.3 | 8.6 |

Example 10

Bioadhesive Spray of Depot Precursor Formulation

A pump spray bottle was found to be a convenient way to apply the formulation topically, e.g. to the skin or the oral mucosa.

A depot precursor formulation prepared as in Example 1 (36% wt PC, 54% wt GDO, and 10% wt EtOH) was sprayed with a pump spray bottle onto the skin and oral mucosa. A film with solid mechanical properties formed shortly after application.

Example 11

Robustness of a Topical Film

After applying the depot precursor formulation, as described in Example 10, (36% wt PC, 54% wt GDO, and 10% wt EtOH) to the skin, the applied formulation was exposed to flushing water (10 L/min) for 10 minutes. The formulation showed excellent bioadhesive properties and resistance against rinsing and no loss of the formulation could be discerned.

Example 12

Formation of Cubic Phase with Solid Properties after Exposure of Depot Precursor Formulation to Air After exposing a depot precursor formulation prepared as described in Example 1 (36% wt PC, 54% wt GDO, and 10% wt EtOH) to air (RT, relative humidity 40%) for at least 3 hours, a solid cubic phase was formed. This formation of a cubic phase structure demonstrates that a topical film will acquire bulk non-lamellar depot properties after application without the need for direct exposure to excess aqueous fluid.

Example 13

Formulation to Treat Periodontitis or Perimplantitis

In order to treat periodontitis or perimplantitis an antibacterial formulation is injected in the periodontal pocket, and a prolonged effect of the formulation is normally desired. 100 µL of a formulation as prepared in Example 1, with the addition of the antibiotic chlorohexidine (PC/GDO/EtOH/chlorhexidine (35/53/10/2)), is injected via a syringe into a rat peridontal pocket. The injected composition is observed to transform from the low viscous formulation, and which initially spreads out to fill voids, to form a solid mass by uptake of gingival fluids. An antibacterial depot system is thus provided.

Chlorhexidine remains at clinically effective levels (MIC 125 µg/ml) in the GCF of the periodontal pockets for over 1 week. The depot system is completely degraded by enzymes within 7 to 10 days and does not need to be removed.

Example 14

Alternate Antibacterial Formulation to Treat Periodontitis or Perimplantitis

An alternate antibacterial formulation was provided by a formulation prepared as described in Example 1 and containing the antibacterial detergent Gardol (Glycine, N-methyl-N-(1-oxododecyl)-, sodium salt) (PC/GDO/EtOH/Gardol (34/51/10/5)). This formulation is injected into the rat periodontal pocket.

Gardol is observed to remain at clinically effective levels in the GCF of the periodontal pockets for a prolonged period (several days). The depot system is completely degraded by enzymes within 7 to 10 days and did not need to be removed.

Example 15

Adhesion of the Formulation to High Energy Surfaces

In order to treat perimplantitis, adhesion not only to biological surfaces but also to high energy surfaces such as a gold or titanium implant is important. It is also important that the formulation adheres to ceramic and plastic surfaces.

A formulation (PC/GDO/EtOH (36/54/10)) as prepared in Example 1 was applied to various surfaces in the oral cavity. The composition showed excellent adhesion to ceramic, plastic, gold, as well as to a normal tooth surface and could not be rinsed away by excess aqueous fluid. The depot resulting from the composition stayed at the site in the oral cavity where it was applied for at least 6 h.

Example 16

Bioadhesive Sustained Release Formulation of Sodium Fluoride for Use on the Teeth Fluoride containing compounds are often needed to oppose caries attack and a bioadhesive formulation precursor with depot effect was prepared as indicated in Example 1 from a mixture of PC/GDO/EtOH/sodium fluoride (35/53/10/2). The formulation was a dispersion of sodium fluoride since it could not be dissolved in the precursor. The liquid formulation was applied to the teeth with the aid of a brush. By uptake of saliva the formulation solidified and formed a depot providing sustained release of sodium fluoride for an extended period (several hours).

Example 17

Oral Cavity Spray Depot Composition

To be suitable as a topical depot system in the oral cavity the mechanical properties of the system was adjusted by decreasing the PC/GDO ratio.

A mixture containing PC/GDO/EtOH (27/63/10) was prepared according to Example 1. A drop of patent blue was added to visualize the formulation after application. About 300 µl of the formulation was sprayed into the oral cavity with pump spray bottle. Shortly after application the formulation viscosified/solidified since it underwent a phase transformation by uptake of aqueous fluid (saliva) and loss of solvent (EtOH). The formulation had excellent bioadhesion to keritinized surfaces such as the hard palate and the gum. Here the film lasted for several hours despite saliva secretion and mechanical wear by the tongue. At soft mucosal surfaces the duration was much shorter (minutes).

Example 18

Oral Cavity Liquid Depot Composition

To be suitable for application with a pipette to the oral cavity the solidification/viscosification of the formulation has to be delayed relative to the spray formulation. This is to allow the formulation to be conveniently distributed with the tongue to a thin film in the oral cavity after application.

Propylene glycol (PG) and EtOH were added to a formulation prepared as in Example 1, to the final composition PC/GDO/EtOH/PG (24/56/10/10). 300 µl of the formulation was conveniently applied with a pipette to the oral cavity and distributed with the tongue to a thin film in the oral cavity. After about 20 seconds the viscosification of the formulation started since it underwent a phase transformation by uptake of aqueous fluid (saliva) and loss of solvent (EtOH and PG). After about one minute the solidification/viscosification appeared to be finished. The formulation had excellent bioadhesion to keritinized surfaces such as the hard palate and the gum. Here the film lasted for several hours despite saliva secretion and mechanical wear by the tongue. At soft mucosal surfaces the duration was much shorter (minutes).

Example 19

Bioadhesive Depot for Nails

The mixture in Example 18 was sprayed to the nail bed and in between the toes. The formulation solidifies/viscosifies slowly by uptake of aqueous fluids (cf. sweat). The solidification can be speeded up by adding water after spray application. The formulation had excellent bioadhesive properties and had a duration for several hours.

Example 20

Loading Capacity of the Bioactive Agent Benzydamine in the Formulation Precursors Formulations with compositions as specified in Table 5 were prepared using the method in Example 1. An excess amount of benzydamine (50 mg) was added to 0.5 g of the formulations. The vials were placed on a shaker at 15° C. for three days after which the solutions were filtered through a filter (0.45 µm) to get rid of crystals of undissolved benzydamine. The benzydamine concentration in each formulation was determined with reversed phase gradient HPLC and UV detection at 306 nm and the results are given in Table 5.

TABLE 5

| Composition GDO/PC(Lipoid S100)/EtOH | Benzydamine concentration in formulation |
| --- | --- |
| 67.5/22.5/10 | 3.4% |
| 63/27/10 | 3.2% |
| 58.5/31.5/10 | 3.3% |
| 60/20/20 | 4.0% |
| 56/24/20 | 4.5% |
| 52/28/20 | 4.3% |

Example 21

Compositions Containing PC and Tocopherol

Depot precursor formulations were prepared with several different PC/α-tocopherol compositions using the method of Example 1 (PC was first dissolved in the appropriate amount of EtOH and thereafter α-tocopherol was added to give clear homogenous solutions).

Each formulation was injected in a vial and equilibrated with excess water. The phase behaviour was evaluated visually and between crossed polarizes at 25° C. Results are presented in Table 6.

TABLE 6

| α-tocopherol | PC | Ethanol | Phase in excess $H_2O$ |
| --- | --- | --- | --- |
| 2.25 g | 2.25 g | 0.5 g | $H_{II}$ |
| 2.7 g | 1.8 g | 0.5 g | $H_{II}/I_2$ |
| 3.15 g | 1.35 g | 0.5 g | $I_2$ |
| 3.6 g | 0.9 g | 0.5 g | $I_2/L_2$ |

Example 22

In Vitro Release of Water-Soluble Disodium Fluorescein

A water-soluble colorant, disodium fluorescein (Fluo), was dissolved in a formulation containing PC/α-tocopherol/Ethanol (27/63/10 wt %) to a concentration of 5 mg Fluo/g formulation. When 0.1 g of the formulation was injected in 2 ml of phosphate buffered saline (PBS) a reversed micellar ($I_2$) phase was formed. The absorbency of Fluo released to the aqueous phase was followed at 490 nm over a period of 3 days. The release study was performed in a 3 mL vial capped with an aluminium fully tear off cap at 37° C. The vial was placed on a shaking table at 150 rpm.

The release of Fluo from the PC/α-tocopherol formulation (see Table 7) indicates that this (and similar) formulations are promising depot systems. Furthermore, the absence of a burst effect is noteworthy, and the release indicates that the substance can be released for several weeks to months; only about 0.4% of Fluo is released after 3 days.

TABLE 7

| Formulation | % release (37° C.) | |
| --- | --- | --- |
| | 24 h | 72 h |
| PC/α-tocopherol/EtOH: 27/63/10 wt % | <0.1* | 0.43 |

*Release below detection limit of the absorbance assay

Example 23

Formulations of the Analgesic/Antiinflammatory Benzydamine

Formulations were prepared as in Example 1 by mixing benzydamine with a mixture of GDO, PC, ethanol and optionally PG/AP in the following proportions.

| Formulation | BZD | GDO | PC | EtOH | PG | AP |
| --- | --- | --- | --- | --- | --- | --- |
| 1 | 3.0 | 53.3 | 28.7 | 10.0 | 5.0 | 0.01 |
| 2 | 3.0 | 53.3 | 28.7 | 15.0 | 0 | 0.01 |
| 3 | 3.0 | 57.4 | 24.6 | 10.0 | 5.0 | 0.01 |
| 4 | 3.0 | 49.2 | 32.8 | 10.0 | 5.0 | 0.01 | where BZD is benzydamine, EtOH is ethanol, PC is LIPOID S100 soybean phosphatidylcholine, GDO is glycerol dioleate, PG is propylene glycol, and AP is ascorbyl palmitate.

All formulations are low viscosity liquids which generate liquid crystalline phase compositions upon exposure to aqueous conditions.

Example 24

Fentanyl Nasal Formulation

Formulations were prepared as in Example 1 by mixing the narcotic analgesic fentanyl with a mixture of GDO, PC, ethanol and optionally PG in the following proportions.

| Formulation | Fentanyl | PC | GDO | EtOH | PG |
| --- | --- | --- | --- | --- | --- |
| 1 | 0.05 | 34 | 51 | 10 | 5 |
| 2 | 0.05 | 36 | 54 | 10 | — |
| 3 | 0.05 | 42 | 43 | 10 | 5 |
| 4 | 0.05 | 45 | 45 | 10 | — |
| 5 | 0.15 | 34 | 51 | 10 | 5 |
| 6 | 0.15 | 36 | 54 | 10 | — |
| 7 | 0.05 | 30 | 45 | 15 | 10 |
| 8 | 0.15 | 30 | 45 | 15 | 10 | where EtOH is ethanol, PC is LIPOID S100 soybean phosphatidylcholine, GDO is glycerol dioleate, and PG is propylene glyco All formulations are low viscosity liquids suitable for administration by nasal spray, which generate liquid crystalline phase compositions upon exposure to aqueous conditions.

Example 25

Diazepam Nasal Formulation

Formulations were prepared as in previous examples by mixing the benzodiazepine antianxiety agent diazepam with a mixture of GDO, PC, ethanol and optionally PG in the following proportions.

| Formulation | Diazepam | PC | GDO | EtOH | PG |
| --- | --- | --- | --- | --- | --- |
| 1 | 5 | 32 | 48 | 10 | 5 |
| 2 | 5 | 34 | 51 | 10 | — |
| 3 | 10 | 37 | 38 | 10 | 5 |
| 4 | 10 | 40 | 40 | 10 | — |
| 5 | 10 | 30 | 45 | 10 | 5 |
| 6 | 10 | 32 | 48 | 10 | — |
| 7 | 10 | 26 | 39 | 15 | 10 |
| 8 | 10 | 30 | 45 | 15 | — | where EtOH is ethanol, PC is LIPOID S100 soybean phosphatidylcholine, GDO is glycerol dioleate, and PG is propylene glycol All formulations are low viscosity liquids suitable for administration by nasal spray, which generate liquid crystalline phase compositions upon exposure to aqueous conditions.

Example 26

Acne Formulations with Clindamycin

Formulations were prepared as in previous examples by mixing the semisynthetic antibiotic clindamycin (free base or salt) with a mixture of GDO, PC, ethanol and PG in the following proportions (by weight).

| Formulation | Clindamycin HCl | PC | GDO | EtOH | PG |
| --- | --- | --- | --- | --- | --- |
| 1 | 1 | 30 | 54 | 10 | 5 |
| 2 | 2 | 29 | 54 | 10 | 5 |
| 3 | 1 | 34 | 50 | 10 | 5 |
| 4 | 2 | 33 | 50 | 10 | 5 |

| Formulation | Clindamycin base | PC | GDO | EtOH | PG |
| --- | --- | --- | --- | --- | --- |
| 5 | 1 | 30 | 54 | 10 | 5 |
| 6 | 2 | 29 | 54 | 10 | 5 |
| 7 | 1 | 33 | 54 | 2 | 10 |
| 8 | 2 | 32 | 54 | 2 | 10 |

The resulting preformulations are low viscosity liquids which, after application resistant to water, sweat, etc. The formulation are applied locally on the skin as a gel or by spraying and are bioadhesive with good film-forming properties.

Example 27

Further Examples of Viscosity in PC/GDO Mixtures on Addition of Co-Solvent

Mixtures of PC/GDO and co-solvent were prepared according to the methods of Example 1 and Example 3 in the proportions indicated in the table below.

The samples were allowed to equilibrate for several days before viscosity measurements were performed using a Physica UDS 200 rheometer at 25° C.

| Sample | PC/GDO (wt/wt) | EtOH/ wt % | Glycerol/ wt % | $H_2O$/ wt % | Viscosity/ mPas |
| --- | --- | --- | --- | --- | --- |
| 1 | 50/50 | 3 | — | — | 1900 |
| 2 | 50/50 | 5 | — | — | 780 |

-continued

| Sample | PC/GDO (wt/wt) | EtOH/ wt % | Glycerol/ wt % | H₂O/ wt % | Viscosity/ mPas |
|---|---|---|---|---|---|
| 3 | 50/50 | 7 | — | — | 430 |
| 4 | 50/50 | 8 | — | — | 300 |
| 5 | 50/50 | 10 | — | — | 210 |
| 6 | 50/50 | 15 | — | — | 100 |
| 7 | 45/55 | 3 | — | — | 1350 |
| 8 | 45/55 | 5 | — | — | 540 |
| 9 | 45/55 | 7 | — | — | 320 |
| 10 | 45/55 | 8 | — | — | 250 |
| 11 | 45/55 | 10 | — | — | 150 |
| 12 | 45/55 | 15 | — | — | 85 |
| 13 | 40/60 | 3 | — | — | 740 |
| 14 | 40/60 | 5 | — | — | 400 |
| 15 | 40/60 | 7 | — | — | 240 |
| 16 | 40/60 | 8 | — | — | 200 |
| 17 | 40/60 | 10 | — | — | 130 |
| 18 | 40/60 | 15 | — | — | 57 |
| 19 | 40/60 | — | 10 | — | $8 * 10^6$ |
| 20 | 40/60 | — | — | 3 | $2.5 * 10^8$ |
| 21 | 40/60 | — | — | 5 | $4 * 10^7$ |

This example further illustrates the need for a solvent with viscosity lowering properties in order to obtain injectable formulations. The mixtures containing glycerol (sample 19) or water (samples 20 and 21) are too viscous to be injectable at solvent concentrations equivalent to the samples containing EtOH (compare with samples 13, 14 and 17).

Example 28

Sunscreen Formulations

Formulations were prepared as in Example 1 by mixing each of several UV absorbing/scattering agents with a mixture of GDO, PC, and ethanol in the following proportions (by weight)

| Formu- lation | PC | GDO | EtOH | Tioveil CM | Spectraveil FIN | Solaveil CT-100 | Tioveil 50 MOTG |
|---|---|---|---|---|---|---|---|
| 1 | 38 | 42 | 5 | — | — | — | 15 |
| 2 | 38 | 42 | 5 | — | — | 15 | — |
| 3 | 37 | 38 | 5 | 15 | 5 | — | — |

Where TIOVEIL CM (Uniqema) comprises Cyclomethicone (and) Titanium Dioxide (and) Dimethicone Copolyol (and) Aluminium Stearate (and) Alumina, SPECTRAVEIL FIN (Uniqema) comprises Zinc Oxide (and) C12-15 Alkyl Benzoate (and) Polyhydroxystearic Acid, SOLAVEIL CT-100 (Uniqema) comprises C12-15 Alkyl Benzoate (and) Titanium Dioxide (and) Polyhydroxystearic Acid (and) Aluminum Stearate (and) Alumina, and TIOVEIL 50 MOTG (Uniqema) comprises Titanium Dioxide (and) Caprylic/Capric Triglyceride (and) Mineral Oil (and) Polyhydroxystearic Acid (and) Aluminum Stearate (and) Alumina.

The resulting formulation precursors show low viscosity upon formulation and are readily applied by pump spray. Upon contact with body surfaces a resilient UV protective layer is formed.

Example 29

Chlorhexidine Periodontal Depots

Formulations were prepared as in Example 1 by mixing the antiinfective agent chlorhexidine digluconate with a mixture of GDO, PC, and ethanol in the following proportions (by weight)

TABLE

Chlorhexidine digluconate depot formulation compositions.

| Formulation | Chlorhexidine digluconate | PC | GDO | EtOH |
|---|---|---|---|---|
| A | 5 | 34 | 51 | 10 |
| B | 5 | 36 | 54 | 5 |
| C | 7 | 33 | 50 | 10 |
| D | 10 | 32 | 48 | 10 |
| E | 15 | 30 | 45 | 10 |

The chlorhexidine depot preformulations have low viscosity and are easily administered to the periodontal pocket. The compositions provide better distribution and spreading of the active substance throughout the periodontal pocket when compared to current products, such as Periochip®.

The depot formed after application gives protection against re-infection of the pocket. The depot also has excellent bioadhesive properties and sticks to mucosal, teeth and bone surfaces.

Release of chlorhexidine digluconate from 250 mg Formulation A (see above) in 0.9% aqueous NaCl (500 ml) was studied. The formulation was held in a cylindrical metal cup which was placed in a teflon holder at the bottom of a standard USP release bath. The contact area between the formulation and surrounding saline solution was 2.4 cm², and the solution was stirred by paddle at 100 rpm.

The release curve shown in FIG. 3 demonstrates the sustained and essentially uniform release of chlorhexidine from the formulation over a period of 24 hours.

Example 30

Topical Formulation with a NSAID

Diclofenac sodium is a nonsteroidal anti-inflammatory drug (NSAID). It belongs to the phenylacetic acid group and is used in inflammatory conditions of various etiologies, degenerative joint disease and many other painful conditions.

A formulation for topical administration containing diclofenac sodium was prepared by first preparing a placebo formulation.

Composition of placebo formulation

| Excipient | Abbreviation | Concentration (%) |
|---|---|---|
| Phosphatidyl choline (from soy bean) | SPC | 45.0 |
| Glycerol dioleate | GDO | 45.0 |
| Etanol 99.5% | EtOH | 10.0 |

Diclofenac sodium to a concentration of 5% was dissolved in the placebo formulation. The resulting oily liquid was slightly yellowish, transparent, and had a low viscosity.

Example 31

Formation of Liquid Crystalline Phase

One drop of the diclofenac sodium containing formulation in Example 30 was added to 3 ml aqueous saline solution with a pipette. A cohesive liquid crystalline phase formed.

Example 32

Formation of Rigid Film In Situ

One drop of the diclofenac sodium containing formulation in example 30 was applied to the skin on the arm of a healthy volunteer and smeared out to a thin film covering an area of about 2-4 cm². Shortly after application the liquid formulation transformed to a much more rigid film by uptake of small amounts of water from the skin and/or the air.

Example 33

Improving Spray Pattern by Lowering Viscosity

A placebo formulation with the composition as given in the Table in Example 30 was filled in a standard pump-spray bottle. After priming the pump with formulation the formulation could be applied to the skin with a sub-optimal spray-pattern. By diluting the formulation further with EtOH the viscosity of the formulation decreased and at an EtOH concentration corresponding to about 25% the formulation could be applied as a mist to the skin. Spaying the formulation to the skin on the arm of a healthy volunteer resulted in formation of a rigid film after evaporation of EtOH and uptake of small amounts of water from the skin and/or the air.

Example 34

Improving Spray Pattern by Using a Compression Pump Device

A placebo formulation with the composition as given in the Table in Example 30 was filled in a standard compression pump bottle. This device gave a good mist/aerosol and spray pattern. Spaying the formulation to the skin on the arm of a healthy volunteer resulted in formation of a rigid film after uptake of small amounts of water from the skin and/or the air.

Example 35

Use of Pressure Driven Device

A placebo formulation with the composition as given in the Table in Example 30 was filled in a pressure driven spray-device either with a hydrocarbon propellant or with HFC-134a as propellant, respectively. Both propellants were found to form low-viscous homogeneous mixtures with the formulation. Spaying the formulation to the skin on the arm of a healthy volunteer resulted in rapid formation of a rigid film after uptake of small amounts of water from the skin and/or the air.

Example 36

Spraying Formulation with Very Low Concentration of EtOH

A formulation with the composition as given in the table below was prepared by evaporating EtOH from the placebo formulation with the composition as given in the Table in Example 30 with the aid of a rotary evaporator (vacuum, 40° C.). The resulting formulation had a high viscosity but when mixed with propellant (hydrocarbon propellant or HFC-134a) and filled in a spray bottle the formulation could be sprayed to the skin on the arm of a healthy volunteer where a rigid film formed after uptake of small amounts of water from the skin and/or the air.

| Composition of placebo formulation | | |
|---|---|---|
| Excipient | Abbreviation | Concentration (%) |
| Phosphatidyl choline (from soy bean) | SPC | 49.0 |
| Glycerol dioleate | GDO | 49.0 |
| Etanol 99.5% | EtOH | 2.0 |

Example 37

Targeting to Different Surfaces by Varying the Composition of the Formulation By varying the PC/GDO ratio in the formulation duration of the formulation at different places in the oral cavity could be adjusted. A formulation with the composition PC/GDO/EtOH (36/54/10) has a preference for adherence to hard surfaces, such as teeth, while a formulation with the composition PC/GDO/EtOH (27/63/10) was found to be better suited for the upper palate.

Example 38

Formation of a Liquid Crystalline Phase from Precursors with Various Solvent Mixtures To improve solubility of active substance in the precursors it may be useful to change solvent in the formulation. A number of different solvent mixtures were used in the formulation precursors (see Table) and their ability to form a liquid crystalline phase after contacting them with excess aqueous solution was investigated. One drop of each formulation was added to 3 ml aqueous saline solution with a pipette. Independent of the solvent (mixture) used a cohesive liquid crystalline phase formed.

| Composition of formulations | |
|---|---|
| Excipients | Composition (wt %) |
| PC/GDO/EtOH | 45/45/10 |
| PC/GDO/EtOH/NMP | 45/45/5/5 |
| PC/GDO/EtOH/propylene-carbonate | 45/45/5/5 |
| PC/GDO/EtOH/dimethyl-isosorbide | 45/45/5/5 |
| PC/GDO/EtOH/dimethyl-acetamide | 45/45/5/5 |
| PC/GDO/EtOH/ethyl-acetate | 45/45/5/5 |

Example 39

Topical Formulation with Testosterone Enanthate

A topical formulation containing 2% testosterone enanthate was prepared by mixing the components in the Table below. Shortly after applying the liquid formulation to the skin it transformed to a much more rigid film by uptake of small amounts of water from the skin and/or the air.

| Composition of topical formulation with testosterone enanthate | | |
|---|---|---|
| Component | Amount (g) | Composition (wt %) |
| Testosterone enanthate | 0.060 | 2.00 |
| Soy Phosphatidyl Choline | 1.323 | 44.10 |
| Glycerol Dioleate | 1.323 | 44.10 |
| Ethanol | 0.294 | 9.80 |

Example 40

Further Studies 40.1—Materials

Excipients used in the experiments of this Example were soy phosphatidylcholine (SPC) denoted as S100 (Lipoid GmbH, Ludwigshafen, Germany); glycerol dioleate (GDO) denoted as Rylo DG 20 Pharma (Danisco, Aarhus, Demark); and polyoxyethylene (20) sorbitan monooleate denoted as polysorbate 80, P80 (Croda, U.K.) Lidocaine (LID) (purity 98%, Lot 068K0112) and triamcinolone acetonide (TCA) (purity 99.5%, Lot 115K1393) were purchased from Sigma-Aldrich. Granisetron hydrochloride (GRN) (purity 99.9%, Batch No 20090914) was obtained from LGM Pharma (Nashville, Tenn.). Benzydamide hydrochloride (BZD) was obtained from Apoteksbolaget AB (Umeå, Sweden). Absolute ethanol (99.5 vol %) from Solveco AB (Rosersberg, Sweden), propylene glycol (PG) from Apoteksbolaget AB (Umea, Sweden), sterile water from B. Braun Medical AB (Bromma, Sweden) and phosphate buffered saline (PBS) tablets yielding 0.01 M phosphate buffer, 0.137 M NaCl, 0.002 M KCl, pH 7.4 from Sigma-Aldrich were used for the preparation of lipid formulations and liquid crystalline (LC) phases. All other solvents and reagents were of analytical grade and were used as received.

40.2—Preparation of Lipid-Based Compositions

Non-aqueous lipid formulations were prepared by mixing appropriate amounts of excipients (for example SPC and/or GDO) and co-solvents (e.g. ethanol and/or propylene glycol (PG)). The samples were then placed on a roller mixer at room temperature for few hours until mixed completely. Active pharmaceutical ingredient (API)-containing formulations were prepared by weighing appropriate amounts API and non-aqueous lipid formulation and placing on a roller mixer at room temperature for 12 hours until homogeneous mixture was obtained. In this Example the concentration of API is always expressed as wt % of the total formulation weight. Prepared lipid compositions were kept at room temperature until further use.

Formulations used in the clinical pilot study (Example 40.7) were manufactured by Apoteket Production and Laboratories AB, Umeå, Sweden, according to Good Manufacturing Practice standards. Study formulations were divided into 3.5-ml aliquots in glass vials sealed with rubber caps. The study formulations were labelled with: "For clinical study," patient number, treatment day, expiry date, storage instructions, investigator name, manufacturer name and sponsor name. Apoteket Production and Laboratories AB also manufactured an ethanol solution of Patent Blue (E 131) (PtB) (Batch No. 1934084) that was added to the study formulations before administration for visualisation purposes. The formulations and stain solution were stored at room temperature (15-25° C.) in the dark at the hospital pharmacy until delivered to the site. On the day of administration, 12 µl of the Patent Blue solution (10% w/w in ethanol) per ml of study formulation was added at the hospital pharmacy in Lund.

Phase Behavior and Nanostructure of Lipid Compositions

Aqueous phase behavior was studied by hydrating non-aqueous lipid formulations with phosphate buffered saline (0.01 M phosphate buffer with 0.137 M NaCl and 0.002 M KCl, pH 7.4) at various weight ratios: 2:1, 1:1, 1:2 and 1:9. After brief vortexing, samples were left to equilibrate at room temperature for 1 week before X-ray diffraction measurements.

The nanostructure of hydrated lipid samples was studied using synchrotron small angle X-ray diffraction (SAXD). Measurements were performed at the 1911 beam-line at MAX-lab (Lund University, Sweden), using a Pilatus 1M 165 mm CCD detector with a resolution of 981×1043 pixels at a pixel size of 0.172 mm. The lipid samples were mounted between kapton windows in a steel sample holder at a sample-to-detector distance of 1312 mm. Diffractograms were recorded at the X-ray wavelength of 0.91 Å and a beam size of 0.25×0.25 mm (full width at the half maximum) at the sample. Temperature control within 0.1° C. was achieved using computer controlled Julabo heating circulator F12-MC (Julabo Labortechnik GMBH, Seelbach, Germany). When temperature effects were studied, the experiments were performed successively at 25° C., 37° C. and 42° C. with a 3-min exposure time at each temperature and a wait of 10 minutes between temperature steps. The resulting CCD images were integrated and analysed using the Fit2D software provided by Dr. A. Hammersley (http://www.esrf.fr/computing/scientific/FIT2D). Silver behanate calibrated sample-to-detector distance and detector positions were used.

40.3—Non-Clinical Assessment of Tolerability of SPC/GDO Formulations in Syrian Hamsters.

Three non-clinical studies in Syrian hamsters were performed assessing local tolerability of SPC/GDO formulations (Camurus A B. Unpublished results, 2005, 2011a, and 2011b). The Syrian hamster was selected as this species is accepted as a suitable model (in compliance with ISO10993-11) for the intended clinical dosing route of Episil® on the oral mucosa. A collar was placed around the neck to permit normal feeding and respiration but preventing the animal from storing food in the pouches, which could damage the cheek pouch mucosa. Prior to administration, the collar was removed and the pouch was rinsed with physiological saline solution. The test items were applied onto the left cheek pouch while the right pouch was left untreated as intra-individual controls. Local tolerability was assessed by visual inspection and scoring using an otoscope prior to each administration and at termination examination, and by histopathology; a 7-day oral irritation study (N=24 females), a 15-day pilot feasibility study (N=10 females) to determine the maximum feasible dose volume and regimen by assessment of bioadhesion, and evaluation of local irritation, and a 90-days subchronic systemic toxicity study (N=40 females and 40 males), applying the maximum feasible dose determined in the pilot study.

The 7-day study evaluated local irritation by macroscopic and microscopic examination of the oral cheek pouches following daily application of 0.5 mL of 4 different test formulations.

In the 15-day study, mucosal adhesion of Episil® dyed with Patent blue after daily and twice-daily exposure onto cheek pouches of up to 0.45 mL (3 sprays of 0.15 mL) was evaluated by otoscopic inspection prior to each administration. Local irritation was assessed by visual inspection and scoring prior to each administration, macroscopic evaluation and scoring at termination and histopathology of the cheek pouches.

The 90-day study was designed to meet the requirements for determining the biocompatibility of a surface-contacting medical device compliant with ISO10993-1. The animals were divided into two treatment groups (Group 1 and Group 2) each including three different termination groups; 5+5 interim animals treated for 28 days, 10+10 main study animals treated for 90 days, and 5+5 recovery animals treated for at least 90 days followed by a 14-day recovery period. The animals in Group 2 received 1 spray of 0.15 ml Episil® in the left cheek pouch twice daily. The animals in Group 1, the control group, were treated in a similar way using sterile saline. The study design included assessment of sub-chronic systemic toxicity (in compliance with ISO10993-11) as well as assessment of oral irritation by histopathological evaluation (in compliance with ISO10993-10) after the twice daily dosing of Episil®. Twice daily administration was chosen as this was shown to give a permanent exposure to Episil® in the cheek pouches of the Syrian hamsters in the pilot feasibility study. Local tolerability was assessed by macroscopic evaluation of the cheek pouch mucosa using an otoscope prior to each administration and as termination examination, and by histopathology. Irritation index for each treatment groups was determined as the average microscopic score for the untreated control cheek pouch subtracted from the average cheek pouch score for the treated cheek pouch. Systemic toxicity was assessed by body weight change, clinical signs, clinical pathology, necropsy evaluations, organ and tissue weights, and histopathology of cheek pouches and any gross lesions.

Compositions of the formulations used in all three non-clinical studies are given in Table 8.

40.4—Clinical Assessment of Intraoral Bioadhesion in Head and Neck Cancer Patients To access the bioadhesive properties of PC/GDO-based formulations such as Episil®, a cross-over, double-blind, randomized pilot study of 4 FluidCrystal® formulations, with varying SPC/GDO ratio and solvent compositions, was conducted in head and neck cancer (HNC) patients undergoing radiotherapy (n=5) at Lund University Hospital. The trial was conducted in accordance with the Declaration of Helsinki and its revisions as well as with the valid local and national laws of Sweden; with the International Conference on Harmonisation (ICH) Harmonised Tripartite Guideline for Good Clinical Practice (E6) issued in July 1996; and with the relevant European Commission Directives. All patients gave written informed consent prior to enrollment. The patients were screened and randomised during week 3-4 of radiotherapy to receive one study formulation on each day (A, B, C or D in Table 9) during 4 consecutive days (Days 1-4) according to a 4-way crossover schedule, allowing a washout night between treatments. On each treatment day, before application of study medication, the status of the oral cavity was checked and the presence of ulcers was recorded. After each application of the formulation, the oral cavity was examined for presence of the formulation on eight areas in the mucosa; four in the palate, one on the inside of each cheek and one on each side of the tongue.

The visual evaluation of the study formulations was carried out by the dental hygienist 5 min., 30 min., 1 hour, 2 hours and 3 hours after application of each formulation. At each interval, the patient was also asked to assess the acceptability of the formulation, such as irritation, taste and degree of comfort. In addition, the patient was asked to estimate the analgesic effect of the study formulations (pain) using a 100 mm visual analogue scale (VAS). Adverse events were recorded on each treatment day and at the follow-up visit on Day 5. The total study duration for all patients was less than 2 weeks. The double-blind design of the study assured a non-biased evaluation and the crossover design made it possible to compare the various formulations within the same patient. No control groups were used in the study.

40.5—Results and Discussion

Phase Behavior and Structural Properties of SPC/GDO LC Phases

The phase behavior of mixtures of SPC and GDO in water is rich in polymorphism (Oradd et al., 1995; Tiberg et al., 2012). As mentioned, the lipid ratios of SPC/GDO mixtures are expressed in wt %. At 25° C. with increasing GDO content, fully hydrated SPC/GDO mixtures in water form the following phase sequence: lamellar ($L_\alpha$)→reversed 2D hexagonal ($H_2$, up to 62.5/37.5)→reversed micellar cubic of Fd3m space group (50/50-45/55)→reversed 3D hexagonal of $P6_3$/mmc space group (42/58-40/60)→unresolved "intermediate" (39/61-37/63)→Fd3m (37/63-22.5/77.5)→reversed micellar solution ($L_2$, from 20/80).

We investigated the aqueous phase behavior of SPC/GDO mixtures prepared at weight ratios of 40/60, 35/65 and 30/70 in more detail. To more closely mimic in vivo conditions, experiments were performed in more physiologically relevant solvent environment and at appropriate temperatures. PBS is here considered as a physiologically relevant solvent since the pH, viscosity and composition closely mimics that of, for example, saliva. FIG. 4 shows SAXD profiles of the fully hydrated LC aggregates formed in SPC/GDO mixtures in large excess of PBS (pH 7.4) as a function of lipid weight ratio and temperature. At 25° C. and at SPC/GDO weight ratios of 30/70 and 35/65, the lipid mixtures form reversed micellar cubic phase. This is nicely shown by the location of the first 15 Bragg peaks at relative positions in ratios of $\sqrt{3}:\sqrt{8}:\sqrt{11}:\sqrt{12}:\sqrt{16}:\sqrt{19}:\sqrt{24}:\sqrt{27}:\sqrt{32}:\sqrt{35}:\sqrt{40}:\sqrt{43}:\sqrt{44}:\sqrt{48}:\sqrt{51}$, which can be indexed as the (111), (220), (311), (222), (400), (331), (422), (511/333), (440), (531), (620), (533), (622), (444), and (711/551) reflections of a face-centered cubic phase of Fd3m crystallographic space group ($Q^{227}$). Reflections are marked with the arrows in FIG. 4a. At the SPC/GDO weight ratio of 40/60, in addition to Fd3m Bragg peaks, other reflections appear indicating different liquid crystalline structure, i.e. different packing of the reversed micelles.

This diffraction pattern cannot be related to a single liquid crystalline (LC) phase and can be interpreted as an intermediate phase between a hexagonally closed-packed reversed micellar and the cubic Fd3m phase. In general, the results show that at room temperature the phase behavior of SPC/GDO mixtures in excess of PBS is very similar to that in excess of water.

As also seen from FIG. 4, the effect of temperature on the nanostructure of the LC phases is lipid weight ratio-dependent (FIGS. 4b and 4c). Thus, at SPC/GDO weight ratio of 40/60, the LC structure remains affected to a minor extent. In contrast, at SPC/GDO weight ratio of 30/70 the structure of the cubic Fd3m phase is very sensitive to the temperature increase. It almost fully transforms into unorganized reversed micellar solution ($L_2$) at 42° C. which is corroborated by the appearance of broad diffuse diffraction peaks showing only some distance correlation between reversed micelles. Only a minor portion of the sample retains Fd3m cubic nanostructure. Importantly, the cubic LC phase formed at the SPC/GDO weight ratio of 35/65 shows moderate temperature dependence. The temperature increase from 25°

C. to 37° C. and 42° C. induces the transformation of only a fraction of the reversed micellar Fd3m cubic arrangement into unorganized micelles. This is shown by the superimposed appearance of both Bragg diffraction peaks from cubic structure and diffuse broad scattering from $L_2$ solution. The calculated lattice parameter (a) for the Fd3m phases is relatively constant for all LC samples regardless of SPC/GDO weight ratio and temperature and only slightly varies between 15.1 and 15.4 nm.

FIG. 5 shows the importance of the nature of the co-solvent used to prepare lipid formulations and their ability to form ordered LC structures upon hydration in PBS at physiologically relevant temperatures. Here the formulations were prepared at the (SPC+GDO)/EtOH/PG weight ratios of 82/3/15, 85/10/5 and 85/15/0 and the SPC/GDO weight ratio was kept constant at 35/65. The SAXD data for all hydrated formulations at 25° C. show essentially identical diffraction patterns of the Fd3m cubic structure. However, at increased temperatures, the hydrated formulation prepared using exclusively EtOH as a solvent shows lower temperature resistance.

Although it sustains more or less ordered Fd3m nanostructure at 37° C., almost complete transformation into unordered $L_2$ solution is observed at 42° C. In contrast, Fd3m LC phases formed from the formulations with high fraction of PG are much more resistant to elevated temperatures and show stronger Bragg peaks from the cubic structure (FIGS. 5b and 5c).

The present Example is focused on the topical use of SPC/GDO LC phases, e.g. with solubilized benzydamine (BZD); therefore some aspects of BZD influence on the phase behavior of lipid mixtures have been investigated. FIG. 6 summarized the SAXD data of the effect of BZD on the nanostructure of LC phases formed in SPC/GDO mixtures as a function of lipid weight ratio (FIG. 6a), BZD concentration (FIG. 6b) and formulation/PBS weight ratio (FIG. 6c). As seen from FIG. 6a, the BZD effect is SPC/GDO weight ratio-dependent. Thus, at high SPC content, the effect of 3 wt % of BZD is minimal and LC phases retain their original nanostructure (FIG. 7). At SPC/GDO weight ratio of 30/70 this effect is much more prominent and the original Fd3m LC phase transforms into $L_2$ solution at 3 wt % of BZD even at 25° C. As shown in FIG. 6b, up to 3.5 wt % of BZD can be entrapped in the cubic phase of SPC/GDO prepared at weight ratio of 35/65 without significantly altering the nanostructure. Interestingly, with increasing BZD concentration, the lattice parameter slightly increases from 15.5 to 16.6 nm as BZD concentration is increased from 0 to 3.5 wt %. At even higher BZD concentration the cubic LC phase transforms into unordered $L_2$ solution. Importantly, the amount of aqueous solution needed for the formation of BZD containing LC phases is rather small. Thus, even at a lipid formulation to PBS weight ratio of 1:1 the cubic Fd3m LC phase is formed (FIG. 6c). Further dilution of the LC phase has no effect on the phase nanostructure and its unit cell dimensions.

40.6—Non-Clinical Assessment of Bioadhesion and Tolerability

The current Example is focused on topical uses of bioadhesive SPC/GDO LC phases at mucosal surfaces. Hence, the importance of local tolerability is eminent. This aspect was investigated in three non-clinical studies in Syrian hamsters: 1) a 7-day oral irritation study (N=24), 2) a 15-day pilot feasibility study assessing bioadhesion determining maximum feasible dose and evaluation of local irritation (N=10), and 3) a 90-day subchronic systemic toxicity study (N=80) of the maximum feasible dose. The 7-day study evaluated the local tolerability of SPC/GDO formulations with and without BZD, while the pilot and the 90-days studies evaluated SPC/GDO formulation without BZD, i.e. Episil® (Table 8). The SPC/GDO ratio of the different formulations was in all cases 35/65, at which all formulations studied formed the reversed micellar ($I_2$) phase of Fd3m structure (FIG. 6b). Note, that the structure formation was not affected by the small compositional variations between formulations, i.e. presence or absence of small amounts of BZD, peppermint oil (PMO) flavor or polysorbate 80 (P80).

TABLE 8

Composition of lipid formulations used for non-clinical assessment of local tolerability and systemic toxicity in Syrian hamsters.

| Study | Composition (weight %) | SPC/GDO weight ratio |
|---|---|---|
| 7-days oral irritation study | SPC/GDO/EtOH/PG 29.7/55.3/10.0/5.0 SPC/GDO/EtOH 29.8/55.2/15.0 SPC/GDO/BZD/EtOH/PG 28.7/53.3/3.0/10.0/5.0 SPC/GDO/BZD/EtOH 28.7/53.3/3.0/15.0 | 35/65 |
| Pilot feasibility study | SPC/GDO/EtOH/PG/PMO 29.47/54.73/10.0/5.0/0.05/0.75 | 35/65 |
| Subchronic systemic toxicity and local irritation study | SPC/GDO/EtOH/PG/PMO 29.47/54.73/10.0/5.0/0.05/0.75 | 35/65 |

In the 7-day study, 0.5 mL of the test formulation was applied to the left cheek pouch daily for 7 days. The treatment generated no or minimal signs of irritation for all 4 tested formulations.

For the 90-day study, dose selection and frequency of dosing was determined in the pilot feasibility study, showing that a dose of 0.15 mL given twice daily provided an apparent 24-hour exposure of the cheek pouch of Syrian hamsters to the SPC/GDO (Episil®) formulation.

In the subchronic study, it was concluded that treatment of male and female Syrian hamsters twice daily for 90 days with Episil® in the cheek pouches resulted in no signs of systemic toxicity or treatment related irritation; no test item (i.e. Episil®)-related clinical signs, and no scores of oral tissue reactions were observed in any of the animals during the 90 days. The test item was seen not to have any influence on the body weight or body weight gain and no test item-related changes in hematology or clinical chemistry parameters were observed. Furthermore, the reactions identified in histopathological evaluation of the cheek pouches were considered to be mild and with no relation to the treatment with Episil®. There was no difference in average group irritation index recorded for cheek pouches treated with Episil® as compared to cheek pouches treated with sterile saline. It was concluded that twice-daily administration at a dose level of 0.15 ml of Episil® per treatment into one cheek pouch for up to 90 days resulted in no signs of systemic toxicity and that Episil® was well tolerated when administered to the oral mucosal membrane. Episil® was suggested to be classified as "not irritating".

40.7—Clinical Assessment of Intraoral Bioadhesion in Head and Neck Cancer Patients Preliminary physicochemical and functional assessments of SPC/GDO LC formulations suggested that optimal spreading and mucoadhesion coincides with the presence of the reversed cubic micellar phase of Fd3m structure at SPC/GDO weight ratio of 35/65. The ratio for best bioadhesion was tested in a small clinical pilot study in 5 head and neck cancer (HNC) patients with a randomized crossover design featuring 4 different formulations with SPC/GDO weight ratios of 40/60, 35/65 and 30/70, as described above (See also Table 9).

TABLE 9

Composition of lipid formulations used for clinical assessment of intraoral bio-adhesion in head and neck cancer patients undergoing radiotherapy.

| Treatment | Composition (weight %) | SPC/GDO weight ratio |
|---|---|---|
| A | SPC/GDO/BZD/EtOH/PG/PtB 28.7/53.3/3.0/10.0/5.0/0.1 | 35/65 |
| B | SPC/GDO/BZD/EtOH/PtB 28.7/53.3/3.0/15.0/0.1 | 35/65 |
| C | SPC/GDO/BZD/EtOH/PG/PtB 24.6/57.4/3.0/10.0/5.0/0.1 | 30/70 |
| D | SPC/GDO/BZD/EtOH/PG/PtB 32.8/49.2/3.0/10.0/5.0/0.1 | 40/60 |

The mean and median percentage presence of treatments A-D at intraoral treatment sites over time, as visually determined by the dental hygienist, is shown in FIG. 7.

All treatments were found to adhere well, with visual mean percentage presence of all formulations at 8 sites in each patient exceeding 50% after 30 minutes of dosing. Notably, formulations A and B with a SPC/GDO ratio of 35/65 showed the highest percentage presence at the different intraoral sites, exceeding 50% after 3 hours. In addition, to showing an apparent maximum of intraoral coverage for the 35/65 ratio, the study also indicated an importance of the solvent composition, with a higher percentage presence for the mixture of ethanol and PG compared to ethanol alone. The highest median percentage coverage of intraoral sites after 3 h. was 87.5%, observed for formulation A.

In addition to the primary objective of the study to identify a formulation with efficient bioadhesion at the oral mucosa of patients for 3 h, the study also evaluated intraoral pain after dosing and patient's subjective acceptance. Mean VAS pain scores after dosing (FIG. 8) indicate that the pain after dosing was generally well managed but tended to increase with time as the protective SPC/GDO LC film was being eroded and visually disappearing. Though formulation A appears to show the lowest mean pain, there were no statistical differences between treatments. The general trend seen in FIG. 8 has been confirmed in a follow up clinical Phase II study in 38 radiation-treated HNC patients, in whom pain scores dropped to minimum values within 5 to 30 min., and then only slowly increased over time for the subsequent 8 hours.

To assess the acceptability of the different SPC/GDO formulations, patients were asked to fill in forms regarding ease of attachment, taste, and degree of comfort. The treatments were perceived as relatively neutral regarding taste and comfort (FIG. 9). No patient stated that formulation A was uncomfortable in the mouth, while formulations B, C and D irritated the mouth in a few patients. Furthermore, all formulations were reported as acceptable when administered. Most of the formulations took less than 1 minute to form a gel, with formulation A showing the fastest time to gel formation. All formulations met the requirement of suitability for further clinical development, the best suited being formulation A with the SPC/GDO ratio of 35/65 and containing 10 wt % ethanol and 5 wt % PG. This ratio was chosen for further clinical development of the Episil® medical device product for the treatment of intraoral pain e.g. in patients with oral mucositis, now registered in EU and US.

40.8—Drug Delivery Aspects of SPC/GDO LC Formulations

One of the important aspects of long-acting formulations is the ability to incorporate relevant amounts of pharmaceutical active ingredients (APIs) and to control their release in vivo, e.g. by retaining the desired cubic nanostructure. We investigated the effect of three selected active pharmaceutical ingredients (APIs), lidocaine (LID), triamcinolone (TCA), and granisetron (GRN), on the nanostructure of the Fd3m cubic phase formed upon hydration of the (SPC+GDO)/EtOH/PG formulation prepared at 85/10/5 weight ratio (FIG. 10). The SPC/GDO weight ratio of 35/65 was kept constant for all formulations.

As shown from FIG. 10a, the formation of the cubic Fd3m phase was not significantly affected by the presence of LID up to a concentration of 1.7 wt %. At 2 wt % of LID the ordered cubic structure began to transform into $L_2$ solution. The calculated lattice parameter only increased slightly from 15.5 to 16.1 nm when LID concentration was increased from 0 to 2 wt %. At a LID concentration slightly lower than 3 wt % the cubic structure was completely lost and the LC phase transformed into unordered $L_2$ solution. The entrapment of rather large amounts of TCA showed very little effect on both the formation and lattice dimensions of the cubic structure of the formulation (FIG. 10b). At even 5 wt % of TCA the Fd3m structure remained unaltered. The Fd3m cubic structure of the hydrated formulation was found to be very sensitive to the presence of GRN (FIG. 10c). At only 0.8 wt % of GRN the superimposed diffuse scattering from $L_2$ solution first appeared and at about 1.5 wt % of GRN the cubic structure completely disappeared. The strong disordering ability of GRN was followed by its influence on the cubic phase unit cell dimensions. Hence, when GRN concentration was increased from 0 to 1 wt % the lattice parameter increased from 15.5 to 16.6 nm. Note, that a very similar effect was also observed in the case of BZD (FIG. 6c).

It may be concluded that all studied APIs have common, albeit relatively small, disordering effect on the nanostructure of hydrated SPC/GDO/EtOH/PG formulation. The formulation can generally accommodate amounts of the 3 APIs at levels that are predicted to be therapeutic if compared with registered pharmaceutical products. The collective observation is that with increasing API concentration the lattice parameter of the Fd3m cubic phase increases to about 16.6 nm, before transforming into the $L_2$ phase. Most likely further unit cell dimension and accommodation increase of the guest molecule is not possible without structural changes, due to the complex cubic packing constraints within the LC structure. After the maximum load of the API is reached, further concentration increase causes transformation of the Fd3m cubic structure into unordered $L_2$. This is a topic for further studies and clinical trials.

40.9—Conclusions

Data from Example 40 show that lipid liquid crystal-forming systems of SPC and GDO effectively adhere at mucosal surfaces in the oral cavity for extended periods of time. Adherence periods are demonstrated to be at least 3 hours post-dosing. This is seen in the clinical pilot study in Head and Neck Cancer patients. The best coverage and overall acceptability was observed for a SPC/GDO ratio of 35/65 but other tested combinations provided coverage for extended periods also. The 35/65 SPC/GDO ratio coincides with the formation of a reversed cubic micellar $I_2$ phase of Fd3m structure.

The topically administered bioadhesive SPC/GDO 35/65 formulations are well tolerated locally and systemically when administered twice daily for up to 90 days. This was demonstrated by extended non-clinical studies in Syrian hamsters.

The present study furthermore explored the influence of added APIs on the phase structure of SPC/GDO compositions. It was concluded in these studies that significant amounts of API with widely different physicochemical properties can be added to the lipid phase without significantly altering the phase behavior.

The APIs benzydamine, lidocaine, triamcinolone and granisetron were chosen as typical examples. They represent a structurally diverse group of active agents but are relevant for intraoral topical application. All tested active agents can be adminstered at clinically relevant concentrations using at dosage volumes well below the studies' maximum dose. It is also seen that increased concentrations of API can be obtained while maintaining structural integrity of the lipid composition. This can be achieved by tuning the lipid composition, to compensate for the API's effect on the phase behavior. In conclusion, the SPC/GDO system, shows great promise for a wide range of medical applications involving administration of an API to a body surface.

LEGENDS TO FIGURES

FIG. 1. Cumulative release of MB from a depot forming a reversed hexagonal $H_{II}$ phase.

FIG. 2. Decrease in viscosity of the depot precursor on addition of solvents. PC/GDO (6/4) is a precursor to a reversed hexagonal $H_{II}$ phase and PC/GDO (3/7) is a precursor to a reversed cubic I2 phase.

FIG. 3: Release of Chlorhexidine from formulation A, see Example 33.

FIG. 4. SAXD profiles of SPC/GDO mixtures in excess PBS as a function of lipid weight ratio at 25 (a), 37 (b), and 42° C. (c) prepared at lipid formulation:PBS weight ratio of 1:2. Arrows in (a) show indexing of the reflections from the reversed micellar Fd3m cubic phase. Explanation is given in the text.

FIG. 5. SAXD profiles of SPC/GDO/EtOH/PG formulations in excess PBS as a function of EtOH/PG weight ratio at 25 (a), 37 (b), and 42° C. (c) prepared at lipid formulation:PBS weight ratio of 1:2. SPC/GDO weight ratio is 35/65 for all samples.

FIG. 6. Effect of 3 wt % of BZD on the liquid crystalline nanostructure as a function of SPC/GDO weight ratio at lipid formulation:PBS weight ratio of 1:2 (a). Effect of BZD concentration on the nanostructure of SPC/GDO liquid crystalline phases prepared at weight ratio of 35/65 (b). Effect of 3 wt % of BZD on the liquid crystalline nanostructure as a function of lipid formulation:PBS weight ratio at SPC/GDO weight ratio weight ratio of 35/65 (c). The lipid/EtOH/PG weight ratio was 85/10/5 for all samples.

FIG. 7. Time dependence of the mean (±SD) (a) and median (b) values of percentage of sites where treatment was present after administration of SPC/GDO/BZD/EtOH/PG formulations prepared at weight ratios of 53.3/28.7/3/10/5 (A), 53.3/28.7/3/15/0 (B), 57.4/24.6/3/10/5 (C), and 49.2/32.8/3/10/5 (D). Number of examined sites in mouth=8 (left and right sides of the upper palate, lower palate, inside of the cheek and tongue), number of patients=5.

FIG. 8. Time dependence of the mean VAS score after administration of lipid formulation. Patient question form: evaluation of the analgesic effect (pain in mouth). Visual analog scale (VAS): 0=no pain, 100=worst imaginable pain. SPC/GDO/BZD/EtOH/PG formulation compositions by weight are: 53.3/28.7/3/10/5 (A), 53.3/28.7/3/15/0 (B), 57.4/24.6/3/10/5 (C), and 49.2/32.8/3/10/5 (D). Number of patients=5.

FIG. 9. Patient reported outcomes regarding taste (a) degree of comfort (b) after dosing of lipid formulations to head and neck cancer patients. Formulation compositions by weight are: 53.3/28.7/3/10/5 (A), 53.3/28.7/3/15/0 (B), 57.4/24.6/3/10/5 (C), and 49.2/32.8/3/10/5 (D). Number of patients=5.

FIG. 10. Effect of lidocaine (a), triamcinolone (b), and granisetron (c) on the nanostructure of SPC/GDO/EtOH/PG liquid crystalline phases. The formulation:PBS weight ratio was 1:2, the SPC/GDO weight ratio was 35/65 and lipid/EtOH/PG weight ratio was 85/10/5 for all samples. The concentration of API is expressed as wt % of the total formulation weight.

The invention claimed is:

1. A pre-formulation comprising a low viscosity mixture of:
    a) 30 to 89% of glycerol dioleate (GDO) and/or a tocopherol;
    b) 10 to 60% of at least one phosphatidylcholine (PC);
    c) 1 to 30% of solvent selected from ethanol, N-methyl pyrrolidone (NMP), and/or isopropanol;
    including at least one bioactive agent is dissolved or dispersed in the low viscosity mixture, said bioactive agent being selected from the group consisting of: corticosteroids, nonsteroidal anti-inflammatory compounds, local inhibitors of inflammatory pathways, phospholipase inhibitors, anti-infectives, cytokines and cytokine inducers/suppressors;
    wherein the pre-formulation has a viscosity of 1 to 1000 mPas at 20° C.; and
    wherein the pre-formulation forms at least one liquid crystalline phase structure upon contact with an aqueous fluid and/or body surface.

2. A pre-formulation as claimed in claim 1 wherein said liquid crystalline phase structure is bioadhesive.

3. A pre-formulation as claimed in claim 1 wherein component a) consists essentially of diacyl glycerols.

4. A pre-formulation as claimed in claim 1 having a molecular solution, $L_2$ and/or $L_3$ phase structure.

5. A pre-formulation as claimed in claim 1 having 35 to 60% by weight a), 20 to 50% by weight b) and 10 to 20% by weight c).

6. A pre-formulation as claimed in claim 1 wherein component c) is ethanol.

7. A pre-formulation as claimed in claim 1 additionally comprising up to 10% by weight of a)+b) of a charged amphiphile.

8. A pre-formulation as claimed in claim 1 wherein said active agent is a corticosteroid.

9. A pre-formulation as claimed in claim 8 wherein said active agent is at least one hydrocortisone type (Group A), acetonide type (Group B), betamethasone type (Group C), or ester type (Group D) corticosteroid.

10. A pre-formulation as claimed in claim 1 wherein said active agent is at least one selected from the group consisting of hydrocortisone, hydrocortisone acetate, cortisone acteate, tixocortol pivalate, prednisolone, methylprednisolone, prednisone, triamcinolone acetonide, triamcinolone alcohol, mometason, amcinonide, budesonide, desonide, fluocinonide, fluocinonide acetonide and halcinonide.

11. A pre-formulation as claimed in claim 1 which is administrable by rinsing, spraying, gargling, as a patch, by suppository or by enema.

12. A pre-formulation as claimed in claim 11 comprising benzydamine or triamcinolone.

13. A topical pre-formulation as claimed in claim 1 suitable for intraoral administration, which forms a bioadhesive, controlled release product, wherein said bioactive agent comprises at least one selected from; benzydamine, triamcinolone, tramadol, Acetaminophen, Ibuprofen, Propoxyphene, Codeine, Dihydrocodein, Hydrocodone, Oxycodone, Nalbuphine, Meperidine, Leverorphanol, Hydromorphone, Oxymorphone, Alfentanil, Fentanyl and Sefentanil.

14. A topical pre-formulation as claimed in claim 1 suitable for intraoral administration for treatment of periodontal and topical infections, wherein the active agent is chlorhexidine gluconate, and where the pre-formulation is applied as a liquid product which forms a surface gel in situ between 1 second and 5 min after application.

15. A topical pre-formulation as claimed in claim 1 suitable for ocular administration, wherein said active agent comprises at least one selected from diclofenac, pilocarpine, levocabastine hydrochloride, ketotifen fumarate, timolol, betaxolol, carteolol, levobunolol, dorzolamide, brinzolamide, epinephrine, dipivefrin, clonidine, apraclonidine, brimonidine, pilocarpine, atanoprost, travoprost, bimatoprost, unoprostone, pilocarpine hydrochloride, dexamethasone, chloramphenicol, indomethacin and triamcinolone.

16. A topical pre-formulation as claimed in claim 1 suitable for dermatological administration, which forms a bioadhesive, controlled release product, wherein the active agent is selected from cosmetic agents, fragrances, flavourings, essential oils UV absorbing agents and mixtures thereof.

17. A method of delivery of a bioactive agent to a human or non-human animal body, this method comprising administering a pre-formulation as claimed in claim 1, whereby to form at least one liquid crystalline phase structure upon contact with an aqueous fluid in vivo following administration.

18. A pre-formulation as claimed in claim 1 wherein component (c) is present at 5 to 30% by weight.

19. A method of treatment or prophylaxis of a human or non-human animal subject comprising administration of a pre-formulation as claimed in claim 1.

20. A method for the treatment of a human or animal subject comprising administration of a pre-formulation as claimed in claim 1.

21. A method as claimed in claim 20 for the treatment of inflammation and/or irritation at a body surface and/or in a body cavity.

22. A method as claimed in claim 21 wherein said inflammation is caused by Crohn's disease, ulcerative collitus or oral mucositis.

23. A method for the treatment of oral mucositis in a human or animal subject comprising administration of a pre-formulation as claimed in claim 1, said composition comprising 40 to 60 wt % GDO, 20 to 35% PC, 5 to 25% ethanol, and 1 to 8% benzydamine or triamcinolone, or a derivative thereof.

* * * * *